US010226648B2

(12) United States Patent
Gebert-Schwarzwaelder et al.

(10) Patent No.: US 10,226,648 B2
(45) Date of Patent: *Mar. 12, 2019

(54) AGENTS FOR DYEING KERATIN FIBRES, CONTAINING AT LEAST ONE DIMERIC, DICATIONIC AZO DYE AND AT LEAST ONE NON-IONIC SURFACTANT

(71) Applicant: Henkel AG & Co. KGaA, Duesseldorf (DE)

(72) Inventors: Antje Gebert-Schwarzwaelder, Neuss (DE); Melanie Moch, Dormagen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/528,539

(22) PCT Filed: Oct. 2, 2015

(86) PCT No.: PCT/EP2015/072774
§ 371 (c)(1),
(2) Date: May 22, 2017

(87) PCT Pub. No.: WO2016/082999
PCT Pub. Date: Jun. 2, 2016

(65) Prior Publication Data
US 2017/0296847 A1    Oct. 19, 2017

(30) Foreign Application Priority Data
Nov. 25, 2014  (DE) .................. 10 2014 223 938

(51) Int. Cl.
A61Q 5/10    (2006.01)
A61Q 5/06    (2006.01)
A61K 8/49    (2006.01)
A61K 8/34    (2006.01)
C09B 44/20   (2006.01)

(52) U.S. Cl.
CPC .............. *A61Q 5/065* (2013.01); *A61K 8/34* (2013.01); *A61K 8/49* (2013.01); *C09B 44/20* (2013.01)

(58) Field of Classification Search
CPC ............. A61Q 5/10; C09B 44/20; A61K 8/49
See application file for complete search history.

(56) References Cited

U.S. PATENT DOCUMENTS

| 4,562,249 | A | 12/1985 | Schwander et al. |
| 4,563,191 | A | 1/1986 | Hahnke et al. |
| 4,607,071 | A | 8/1986 | Haehnke et al. |
| 7,407,516 | B2 | 8/2008 | Vidal |
| 2001/0001333 | A1 | 5/2001 | Samain |
| 2004/0200009 | A1* | 10/2004 | Vidal .................... C09B 44/126 8/405 |
| 2004/0244124 | A1 | 12/2004 | Plos et al. |
| 2005/0235433 | A1 | 10/2005 | Rondeau |
| 2006/0112502 | A1 | 6/2006 | Cotteret et al. |
| 2012/0325261 | A1 | 12/2012 | Hashimoto et al. |
| 2014/0101868 | A1* | 4/2014 | Hoffmann .............. A61K 8/891 8/407 |
| 2014/0165301 | A1* | 6/2014 | Schweinsberg ........ A61K 8/898 8/409 |
| 2014/0289970 | A1 | 10/2014 | Gross et al. |

FOREIGN PATENT DOCUMENTS

| CA | 2303209 A1 | 3/1999 |
| DE | 2822912 A1 | 11/1979 |
| DE | 4128490A A1 | 3/1993 |
| EP | 0531943 A1 | 3/1993 |
| EP | 1609456 A1 | 12/2005 |
| EP | 1483334 B1 | 7/2007 |
| EP | 1448156 B1 | 8/2007 |
| FR | 2915681 A1 | 11/2008 |
| GB | 910121 A | 11/1962 |
| GB | 1186753 A | 4/1970 |
| GB | 1189753 A | 4/1970 |
| WO | 02100369 A2 | 12/2002 |

OTHER PUBLICATIONS

STIC Search Report dated Aug. 6, 2017.*
EPO, International Search Report and Written Opinion issued in International Application No. PCT/EP2015/072774, dated Nov. 23, 2015.
EPO, International Search Report and Written Opinion issued in International Application PCT/EP2015/072773, dated Nov. 12, 2015.
Preliminary Amendment for U.S. Application entitled "Agents for Dyeing Keratin Fibers, Containing at Least One Dimeric, Dicationic Azo Dye and at Least One Anionic Surfactant".
Substitute Specification for U.S. Application entitled "Agents for Dyeing Keratin Fibers, Containing at Least One Dimeric, Dicationic Azo Dye and at Least One Anionic Surfactant".
EPO, International Search Report and Written Opinion issued in International Application PCT/EP2015/073779, dated Nov. 30, 2015.
Preliminary Amendement for U.S. Application entitled "Agents for Dyeing Keratin Fibres, Containing at Least One Dimeric, Dicationic Azo Dye With Special Substitution Pattern".
Substitute Specification for U.S. Application entitled "Agents for Dyeing Keratin Fibres, Containing at Least One Dimeric, Dicationic Azo Dye With Special Substitution Pattern".
EPO, International Search Report and Written Opinion issued in International Application PCT/EP2015/073775, dated Dec. 1, 2015.
Preliminary Amendment for U.S. Application entitled "Agents for Dyeing Keratin Fibers, Containing at Least One Dimeric, Dicationic Azo Dye and at Least One Anionic and/or Cationic Surfactant".
Substitute Specification for U.S. Application entitled "Agents for Dyeing Keratin Fibers, Containing at Least One Dimeric, Dicationic Azo Dye and at Least One Anionic and/or Cationic Surfactant".
EPO, International Search Report and Written Opinion issued in International Application No. PCT/EP2015/073776, dated Nov. 30, 2015.

(Continued)

*Primary Examiner* — Eisa B Elhilo
(74) *Attorney, Agent, or Firm* — Lorenz & Kopf, LLP

(57) ABSTRACT

The present disclosure relates to agents for dyeing keratin fibres, in particular human hair, containing, in a cosmetic carrier (a) at least one direct dye of formula (I), and (b) at least one non-ionic surfactant.

7 Claims, No Drawings

(56) References Cited

OTHER PUBLICATIONS

Preliminary Amendment for U.S. Application entitled "Agents for Dyeing Keratin Fibers, Containing at Least One Dimeric, Ring-Bridged Azo Dye".
Substitute Specification for U.S. Application entitled "Agents for Dyeing Keratin Fibers, Containing at Least One Dimeric, Ring-Bridged Azo Dye".
USPTO, Office Action in U.S. Appl. No. 15/528,529 dated Aug. 31, 2017.
USPTO, Office Action in U.S. Appl. No. 15/528,538 dated Aug. 30, 2017.
USPTO, Office Action in U.S. Appl. No. 15/528,530 dated Aug. 31, 2017.
USPTO, Office Action in U.S. Appl. No. 15/528,532 dated Aug. 31, 2017.
STIC Search Report dated Jul. 29, 2017, U.S. Appl. No. 15/528,529.
STIC Search Report dated Jul. 2, 2017, U.S. Appl. No. 15/528,538.
STIC Search Report dated Aug. 1, 2017, U.S. Appl. No. 15/528,530.
STIC Search Report dated Jun. 28, 2017, U.S. Appl. No. 15/528,532.

\* cited by examiner

AGENTS FOR DYEING KERATIN FIBRES, CONTAINING AT LEAST ONE DIMERIC, DICATIONIC AZO DYE AND AT LEAST ONE NON-IONIC SURFACTANT

CROSS-REFERENCE TO RELATED APPLICATION

This application is a U.S. National-Stage entry under 35 U.S.C. § 371 based on International Application No. PCT/EP2015/072774, filed Oct. 2, 2015, which was published under PCT Article 21(2) and which claims priority to German Application No. 10 2014 223 938.9, filed Nov. 25, 2014, which are all hereby incorporated in their entirety by reference.

TECHNICAL FIELD

The present disclosure relates to agents for dyeing keratinic fibers, in particular human hair, which contain (a) at least one dimeric, dicationic azo dye of a special formula (I) in combination with (b) at least one nonionic surfactant.

BACKGROUND

It emerged that the color intensity of cationic azo dyes, in particular of the special azo dyes of the formula (I), can be increased by the use of special nonionic surfactants (b). A further subject of the present disclosure, therefore, is the use of nonionic surfactants (b) to improve the substantivity of cationic azo dyes, in particular the special azo dyes of the formula (I), on keratinic fibers.

Either direct dyes or oxidation dyes are generally used for dyeing keratinic fibers. In fact, intense colors with good fastness properties can be achieved with oxidation dyes but the development of the color generally occurs under the effect of oxidizing agents such as, e.g., H2O2, which in some cases can result in damage to the fiber. Furthermore, some oxidation dye precursors or specific mixtures of oxidation dye precursors can have a sensitizing effect in individuals with sensitive skin. Direct dyes are applied under more gentle conditions. Their disadvantage, however, is that the colors often have only insufficient fastness properties.

Depending on the desired coloring result, the skilled artisan uses direct dyes from different dye classes. The direct dyes known from the prior art belong, for example, to the class of nitro dyes, anthraquinone dyes, azo dyes, triarylmethane dyes, or methine dyes. All of these dye classes are intended to fulfill a specific requirements profile for use in the cosmetics sector. Thus, direct dyes should provide an intense coloring result and have fastness properties as good as possible. The coloring result obtained with direct dyes should be influenced as little as possible by environmental effects; i.e., the dyes should possess, for example, good wash fastness, light resistance, and rubbing fastness. Chemical effects as well, to which the keratinic fibers can be exposed after the coloring process (such as, for example, permanents), should change the coloring result as little as possible.

To achieve a lightening as well simultaneously with the dyeing, if possible the direct dyes should also be compatible with the oxidizing agents typically used in blonding processes (such as, e.g., hydrogen peroxide and/or persulfates).

Cationic azo dyes have emerged as a dye class with an excellent requirements profile. Azo dyes are characterized in general by a high stability. Moreover, cationic azo dyes because of their positive charge have a high affinity for keratinic fibers, which depending on the degree of their damage can be charged more or less highly negatively.

If keratinic fibers are to be lightened or blonded oxidatively, direct dyes can also be used in combination with oxidizing agents. Normally aqueous hydrogen peroxide solutions, either alone or in combination with other oxidizing agents acting as bleach activators, such as, for example, persulfate salts, are applied to keratin fibers for blonding hair. To achieve a sufficient blonding effect, agents of this kind are usually adjusted to be highly alkaline, and the pH value in this case is normally between 9 and 10.5. The melanins, the natural, color-imparting pigments of the hair fiber, are destroyed oxidatively by the action of the oxidizing agents and a decoloration or lightening of the fibers is achieved in this manner. The melanins are localized in the cortex of the hair fiber and can be classified in two pigment classes. Eumelanins represent the first, brownish-black class of pigments, whereas the reddish pigments with a higher sulfur content are known as pheomelanins. Due to the different levels of resistance of the various pigment types to oxidizing agents, however, the pheomelanins and eumelanins are not always uniformly decolorized. In addition, in darker hair with an elevated melanin content, the melanins may only be partially or incompletely broken down, so that a residual proportion of the color-imparting pigments remains in the hair after blonding. In these cases, the residual content of melanins still present in the hair after the oxidative process results in a yellowish to reddish shift in shade. Therefore, in particular when darker hair is blonded, a color shift towards warm (reddish) tints occurs.

Users do not normally desire such color shifts towards warm tints. This color shift is therefore usually counteracted by tinting in the corresponding complementary color. The aim here is to achieve a silvery cool appearance of the bleaching result. A skilled artisan refers to this as delustering.

Blue direct dyes in particular may be used for delustering blond shades with an orange cast. For the most complete possible attenuation of the orange color appearance, it is advantageous for the blue dye itself to have no red content in its coloring. Dyes in pure blue shades are therefore better suited to delustering an orange blonding result in comparison with blue dyes with a violet cast.

Within the group of blue direct dyes that can be used in marketed products, there are only very few representatives that allow dyeing in pure blue shades and do not leave behind a color appearance with a violet cast. No dyes are known from the prior art that optimally meet all the aforementioned requirements. There still is accordingly a major need for stable dyes that dye the keratinic fibers in pure blue shades and produce an intense coloring result with excellent fastness properties.

Monomeric cationic azo dyes sufficiently known from the prior art are, for example, the representatives: Basic Orange 31 (alternative name: 2-[(4-aminophenyl)azo]-1,3-dimethyl-1H-imidazolium chloride, CAS No. 97404-02-9) and Basic Red 51 (alternative name: 2-[((4-dimethylamino)-phenyl)azo]-1,3-dimethyl-1H-imidazolium chloride, CAS No. 77061-58-6).

Both dyes dye keratinic fibers with an excellent color intensity in the orange to red shade range. There still is a need, furthermore, for direct blue dyes that are optimally compatible with these two dyes.

BRIEF SUMMARY

Agents for dyeing keratinic fibers and methods for improving the substantivity of cationic azo dyes on keratinic fibers are provided herein. In an exemplary embodiment, an agent for dyeing keratinic fibers includes, in a cosmetic carrier, (a) at least one direct dye of the formula (I),

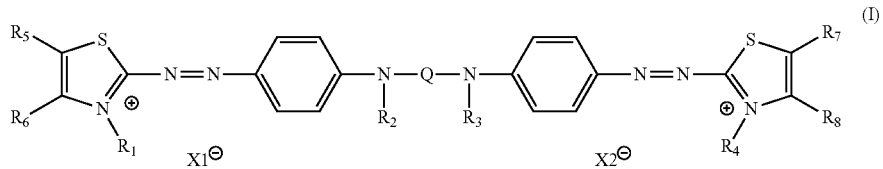

where
- R1, R4 independently of one another stand for a $C_1$-$C_6$ alkyl group, a $C_2$-$C_6$ alkenyl group, a hydroxy-$C_2$-$C_6$ alkyl group, a cyano-$C_1$-$C_6$ alkyl group, a halogen-$C_1$-$C_6$ alkyl group, an aryl-$C_1$-$C_6$ alkyl group, a heteroaryl-$C_1$-$C_6$ alkyl group, an aryl group, or a heteroaryl group,
- R2, R3 independently of one another stand for a hydrogen atom, $C_1$-$C_6$ alkyl group, a $C_2$-$C_6$ alkenyl group, a hydroxy-$C_2$-$C_6$ alkyl group, a cyano-$C_1$-$C_6$ alkyl group, a halogen-$C_1$-$C_6$ alkyl group, an aryl-$C_1$-$C_6$ alkyl group, a heteroaryl-$C_1$-$C_6$ alkyl group, an aryl group, or a heteroaryl group,
- R5, R6, R7, R8 independently of one another stand for a hydrogen atom, a $C_1$-$C_6$ alkyl group, a halogen atom from the group comprising chlorine, bromine, fluorine, or iodine, or for a $C_1$-$C_6$ alkoxy group,
- X1, X2 independently of one another stand for a physiologically acceptable anion, chloride, bromide, iodide, methyl sulfate, methyl sulfonate, p-toluenesulfonate, acetate, hydrogen sulfate, ½ sulfate, or ¼ tetrachlorozincate,
- Q stands for a grouping of the formula (II), (III), (IV), or (V),

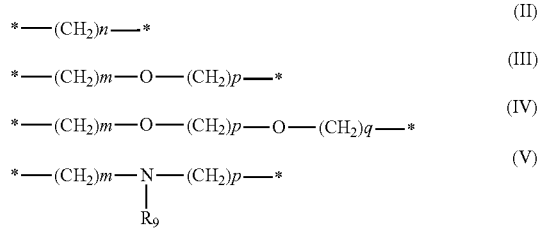

n stands for an integer from 3 to 6,
m, p, q each independently of one another stand for the numbers 2 or 3,
R9 stands for a hydrogen atom, for a $C_1$-$C_6$ alkyl group, for a $C_2$-$C_6$ alkenyl group, or for a hydroxy-$C_2$-$C_6$ alkyl group, and
(b) at least one nonionic surfactant.

In another exemplary embodiment, a method or improving the substantivity of cationic azo dyes on keratinic fibers is provided. The method includes using one or more nonionic surfactants (b) of the formula (B1)

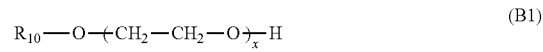

where
R10 stands for a linear or branched $C_{12}$-$C_{30}$ alkyl group and
x stands for an integer from 2 to 100,
for improving the substantivity of cationic azo dyes on keratinic fibers.

DETAILED DESCRIPTION

The following detailed description is merely exemplary in nature and is not intended to limit the present disclosure or the application and uses of the subject matter as described herein. Furthermore, there is no intention to be bound by any theory presented in the preceding background or the following detailed description.

Therefore, it was the object of the present disclosure to find dyes based on direct dyes, which fulfill the typical fastness requirements, imposed on these agents, and which are capable of dyeing keratinic fibers in a pure blue tint without a red content. The colors achievable with these agents should have an especially high color intensity.

Moreover, the blue dyes contained in the agents should also be especially highly compatible with the cationic azo dyes Basic Orange 31 and Basic Red 51.

It could now be found surprisingly that this object is fulfilled to an excellent extent, if dyes of the formula (I), described hereinafter, in combination with at least one nonionic surfactant are used in agents for dyeing keratinic fibers.

A first subject of the present disclosure is an agent for dyeing keratinic fibers, in particular human hair, containing in a cosmetic carrier,
(a) at least one direct dye of the formula (I),

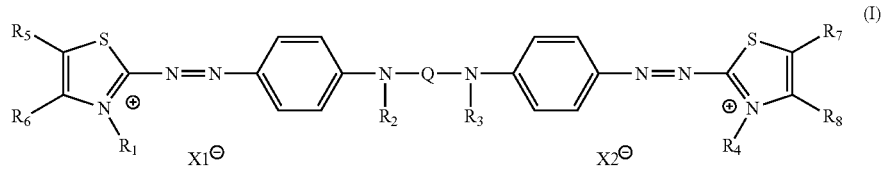

where
R1, R4 independently of one another stand for a $C_1$-$C_6$ alkyl group, a $C_2$-$C_6$ alkenyl group, a hydroxy-$C_2$-$C_6$ alkyl group, a cyano-$C_1$-$C_6$ alkyl group, a halogen-$C_1$-

C$_6$ alkyl group, an aryl-C$_1$-C$_6$ alkyl group, a heteroaryl-C$_1$-C$_6$ alkyl group, an aryl group, or a heteroaryl group, R2, R3 independently of one another stand for a hydrogen atom, C$_1$-C$_6$ alkyl group, a C$_2$-C$_6$ alkenyl group, a hydroxy-C$_2$-C$_6$ alkyl group, a cyano-C$_1$-C$_6$ alkyl group, a halogen-C$_1$-C$_6$ alkyl group, an aryl-C$_1$-C$_6$ alkyl group, a heteroaryl-C$_1$-C$_6$ alkyl group, an aryl group, or a heteroaryl group, R5, R6, R7, R8 independently of one another stand for a hydrogen atom, a C$_1$-C$_6$ alkyl group, a halogen atom from the group comprising chlorine, bromine, fluorine, or iodine, or for a C$_1$-C$_6$ alkoxy group, X1, X2 independently of one another stand for a physiologically acceptable anion, preferably from the group comprising chloride, bromide, iodide, methyl sulfate, methyl sulfonate, p-toluenesulfonate, acetate, hydrogen sulfate, ½ sulfate, or ½ tetrachlorozincate, Q stands for a grouping of the formula (II), (III), (IV), or (V),

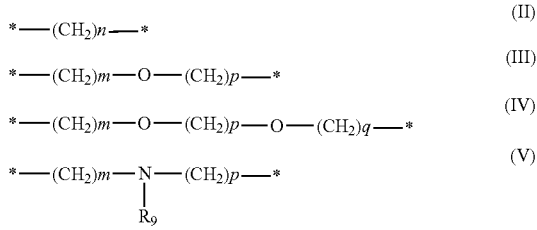

n stands for an integer from 3 to 6, m, p, q each independently of one another stand for the numbers 2 or 3, R9 stands for a hydrogen atom, for a C$_1$-C$_6$ alkyl group, for a C$_2$-C$_6$ alkenyl group, or for a hydroxy-C$_2$-C$_6$ alkyl group, and (b) at least one nonionic surfactant.

Keratinic fibers, keratin-containing fibers, or keratin fibers are to be understood to mean pelts, wool, feathers, and in particular human hair. Although the agents of the present disclosure are primarily suitable for lightening keratin fibers, in principle nothing precludes a use in other fields as well.

The phrase used according to the present disclosure "dyeing of keratin fibers" comprises any form of color modification of the fibers. In particular, color modifications covered by the terms tinting, blonding, delustering, oxidative dyeing, semipermanent dyeing, permanent dyeing, and temporary dyeing are included. Color modifications according to the present disclosure which have a lighter coloring result than the initial color, such as, for example, blonding with coloring, are explicitly also included. The term "delustering of keratin fibers" is understood to mean counteracting undesired shifts in shade which occur during the oxidative color modification of keratin fibers, in particular during blonding or bleaching processes. The aim of delustering is to attenuate the orange to reddish color appearance caused by incomplete blonding and to produce a silvery cool perceived color after the blonding process. The active substances used in delustering may be applied in the form of an aftertreatment step after blonding or bleaching of the keratin fibers. It is likewise possible, however, to apply the active substances used for delustering to the keratin fibers in the course of a single-stage method together with the blonding agent or the bleaching agent. Direct dyes, either alone or in the dye mixture, having suitable color properties, may be used as active substances suitable for delustering. It is likewise possible, furthermore, to use direct dyes in combination with oxidation dye precursors (developers and couplers) for delustering.

The agents of the present disclosure contain the direct dyes of the formula (I) in a cosmetic carrier. Said cosmetic carrier is preferably aqueous, alcoholic, or aqueous-alcoholic. For the purpose of hair treatment, such carriers are, for example, creams, emulsions, gels, or surfactant-containing foaming solutions as well, such as, for example, shampoos, foam aerosols, or other preparations suitable for use on hair. It is also possible, however, for storage purposes to provide a powdered or tablet-shaped preparation as well. Said preparation is then mixed prior to use in an aqueous solvent or with organic solvents or with mixtures of water and organic solvents to obtain the mixture for use. An aqueous carrier in the context of an exemplary embodiment of the present disclosure contains at least 40% by weight, particularly at least 50% by weight of water. Aqueous-alcoholic carriers in the context of the present disclosure are understood to be water-containing compositions containing 3 to 70% by weight of a C1-C4 alcohol, particularly ethanol or isopropanol. The agents of an exemplary embodiment of the present disclosure can contain in addition further organic solvents such as, for example, 4-methoxybutanol, ethyl diglycol, 1,2-propylene glycol, n-propanol, n-butanol, n-butylene glycol, glycerol, diethylene glycol monoethyl ether, and diethylene glycol mono-n-butyl ether. In this case, all water-soluble organic solvents are preferred. Preferred agents of an exemplary embodiment of the present disclosure are characterized in that they contain in addition a nonaqueous solvent, wherein preferred agents of the embodiment contain the solvent in a concentration of about 0.1 to about 30% by weight, preferably in a concentration of about 1 to about 20% by weight, very particularly preferably in a concentration of about 2 to about 10% by weight, based in each case on the agent.

The agents in an accordance with an exemplary embodiment of the present disclosure contain as the first essential ingredient (a) at least one direct dye of the formula (I).

The substituents R1 to R9 of the compounds of the formula (I) are described hereafter by way of example: Examples of a C1-C6 alkyl group are the groups: methyl, ethyl, propyl, isopropyl, n-butyl, s-butyl and t-butyl, n-pentyl, and n-hexyl. Propyl, ethyl, and methyl are preferred alkyl groups. Examples of a C2-C6 alkenyl group are vinyl, allyl, but-2-enyl, but-3-enyl, and isobutenyl; preferred C2-C6 alkenyl groups are vinyl and allyl. Preferred examples of a hydroxy-C1-C6 alkyl group are a hydroxymethyl, a 2-hydroxyethyl, a 2-hydroxypropyl, a 3-hydroxypropyl, a 4-hydroxybutyl group, a 5-hydroxypentyl, and a 6-hydroxyhexyl group; a 2-hydroxyethyl group is particularly preferred. Preferred examples of cyano-C1-C6 alkyl groups are the cyanomethyl group, the 2-cyanoethyl group, and the 3-cyanopropyl group. Halogen-C1-C6 alkyl groups preferred according to an exemplary embodiment are the chloromethyl group, the bromomethyl group, the fluoromethyl group, the 2-chloroethyl group, the 2-bromoethyl group, the 2-fluoromethyl group, the 2-chloropropyl group, the 2-bromopropyl group, the 2-fluoropropyl group, the 3-chloropropyl group, the 3-bromopropyl group, and the 3-fluoropropyl group. Preferred examples of aryl-C1-C6 alkyl groups are benzyl, 1-phenethyl, and 2-phenylethyl. The imidazol-1-ylmethyl group, the imidazol-2-ylmethyl group, the imidazol-4-ylmethyl group, the pyridin-2-yl group, the pyridin-3-yl group, and the pyridin-4-ylmethyl group can be named by way of example for heteroaryl-C1-C6 alkyl groups. Aryl groups preferred according to an exemplary embodiment of the present disclosure are the phenyl group and the naphthyl group. Examples of a heteroaryl group are the pyridin-2-yl group, the pyridin-3-yl group, the pyridin-4-yl group, the imidazol-1-yl group, the imidazol-2-yl group, and the imidazol-4-yl group. Halogen atoms are selected from the group comprising chlorine, bromine, fluorine, and/or iodine, chlorine and bromine being particularly preferred in this case. The methoxy, ethoxy, and propoxy group can be named as examples of a C1-C6 alkoxy group.

The compounds of the general formula (I) carry the R1 and R4 groups; in this case R1 and R4 can be identical or different. The R1 and R4 groups are preferably the same. Preferably, R1 and R4 independently of one another stand for a C1-C6 alkyl group or for a C2-C6 alkenyl group. Particularly preferably, R1 and R4 independently of one another stand for a C1-C6 alkyl group, in particular for a methyl group or for an ethyl group.

Furthermore, the compounds of the general formula (I) carry the R2 and R3 groups; in this case R2 and R3 can be identical or different. The R2 and R3 groups are preferably the same. Preferably, R2 and R3 independently of one another stand for a hydrogen atom, a C1-C6 alkyl group, or for a C2-C6 alkenyl group. Particularly preferably, R2 and R3 independently of one another stand for a hydrogen atom or a C1-C6-alkyl group. Very particularly preferably, R2 and R3 independently of one another stand for a hydrogen atom, a methyl group, or an ethyl group.

Furthermore, the compounds of the general formula (I) carry the R5, R6, R7, and R8 groups; in this case, the R5 to R8 groups can be identical or different. Preferably, the R5, R6, R7, and R8 groups independently of one another stand for a hydrogen atom, a halogen atom, or a C1-C6 alkoxy group. Particularly preferably, the R5, R6, R7, and R8 groups all stand for a hydrogen atom.

In a very particularly preferred embodiment, an agent of the present disclosure is characterized in that it contains (a) at least one direct dye of the general formula (I), in which R1, R4 independently of one another stand for a $C_1$-$C_6$ alkyl group,
R2, R3 independently of one another stand for a hydrogen atom or for a $C_1$-$C_6$ alkyl group,
R5, R6, R7, R8 each stand for a hydrogen atom.

In a very particularly preferred embodiment, an agent of the present disclosure is characterized in that it contains (a) at least one direct dye of the general formula (I), in which R1, R4 independently of one another stand for a methyl group or for an ethyl group,
R2, R3 independently of one another stand for a hydrogen atom, a methyl group, or for an ethyl group, and
R5, R6, R7, R8 each stand for a hydrogen atom.

The dyes of an exemplary embodiment of the present disclosure of the formula (I) are dimeric azo dyes that have a double positive charge. The two positive charges are neutralized by the anionic counterions X1 and X2. In this case, the dicationic organic part is responsible for the blue dyeing of keratin fibers. The counterions X1 and X2 are used only to preserve the electroneutrality, so that the precise nature of the counterions X1 and X2 plays no major role for achieving the desired coloring result. Because the dye is used in a cosmetic agent, the counterions X1 and X2 must be physiologically acceptable. Physiologically acceptable in this context means suitable for use in the cosmetic agent (i.e., for use on human hair and human skin). X1 and X2 are physiologically acceptable anions, preferably from the group comprising chloride, bromide, iodide, methyl sulfate, methyl sulfonate, p-toluenesulfonate, acetate, hydrogen sulfate, ½ sulfate, and ½ tetrachlorozincate. Chloride is understood to be an anion Cl—. Bromide is understood to be an anion Br—. Iodide is understood to be an anion I—. Methyl sulfate is understood to be an anion H3COSO4-.

Methyl sulfonate is understood to be an anion H3CSO3-. p-Toluenesulfonate is understood to be an anion H3C(C6H4)SO3-. Acetate is understood to be an anion H3CCOO—. Hydrogen sulfate is understood to be an anion HSO4-.

½ sulfate is understood to be half an equivalent of the doubly negatively charged anion SO42-. ½ tetrachlorozincate is understood to be half an equivalent of the doubly negatively charged anion ZnCl42-. It is therefore likewise possible in the case of the sulfate and tetrachlorozincate and also according to an exemplary embodiment of the present disclosure, if the dicationic dye of the formula (I) is neutralized by a SO42- ion or by a ZnCl42- ion.

The grouping Q is a grouping that links the two singly positively charged chromophores of the dye to the dicationic dimer. Q stands for a grouping of the formula (II), (III), (IV), or (V),

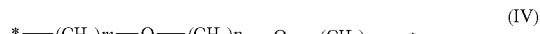
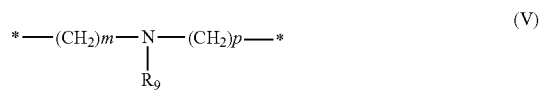

n stands for an integer from 3 to 6,
m, p, q each independently of one another stand for the numbers 2 or 3, and
R9 stands for a hydrogen atom, for a $C_1$-$C_6$ alkyl group, for a $C_2$-$C_6$ alkenyl group, or for a hydroxy-$C_2$-$C_6$ alkyl group.

The two positions labeled with an asterisk in this case each represent the linkage positions to the two N atoms of the formula (I).

It emerged surprisingly as fundamentally important and essential to an exemplary embodiment of the present disclosure for achieving an intense coloring result that the linking grouping Q, linking the two azo chromophores, has a chain length of at least 3 atoms. For this reason, n in the formula (II) stands for an integer of at least 3. The linking grouping Q of the formula (II) therefore comprises at least 3 C atoms (i.e., here this is a grouping with the minimum length of —CH2-CH2-CH2-).

In the formula (III), m and p each stand for an integer of at least 2, so that this linking grouping has in total a chain length of at least 5 C and O atoms (i.e., here this is a grouping with the minimum length of —CH2-CH2-O—CH2-CH2-).

In the formula (IV), m, p, and q each stand for an integer of at least 2, so that this linking grouping in a similar way has a chain length of at least 8 C and O atoms (i.e., here this is a grouping with the minimum length of —CH2-CH2-O—CH2-CH2-O—CH2-CH2-).

Analogously, in the formula (V) as well, m and p stand for integers of at least 2, so that this linking grouping as well has a chain length of at least 5 C and N atoms.

Within the scope of comparison tests, it emerged that dimeric azo dyes of the principal type of the formula (I), which, however, do not have a linker group Q as described in the present disclosure with a length of only 2 C atoms, have an extremely poor substantivity on the keratin fibers.

Whereas intense colors with a deep dark-blue shade could be achieved with the dye of the formula (I) in accordance with an exemplary embodiment of the present disclosure, dyeing with analogous dimeric dyes, which are linked via a shorter Q grouping with a chain length of only 2 C atoms, led to virtually no color absorption at all on the keratinic fibers.

Without being restricted to a theory, a rigid geometry associated with the short linker chain Q and an unfavorable spatial conformation of the dye caused by this could perhaps worsen the diffusion of the short-chain dimeric dyes into the keratinic fiber.

Within the Q groupings of the formulas (II), (III), (IV), and (V), the best coloring results and the most intense colors could be achieved with the grouping of the formula (II).

In a very particularly preferred embodiment, an agent of the present disclosure is characterized in that it contains (a) at least one direct dye of the general formula (I), in which Q stands for a grouping of the formula (II), $$*—(CH_2)n-* \quad (II)$$

and n stands for an integer from 3 to 6.

In an explicitly very particularly preferred embodiment, an agent of the present disclosure is characterized in that it contains (a) at least one dye of the general formula (I), in which Q stands for a grouping of the formula (II), $$*—(CH_2)n-* \quad (II)$$

and n stands for the number 3.

In a further preferred embodiment, an agent for dyeing keratinic fibers is characterized in that it contains at least one compound of the general formula (I), which is selected from

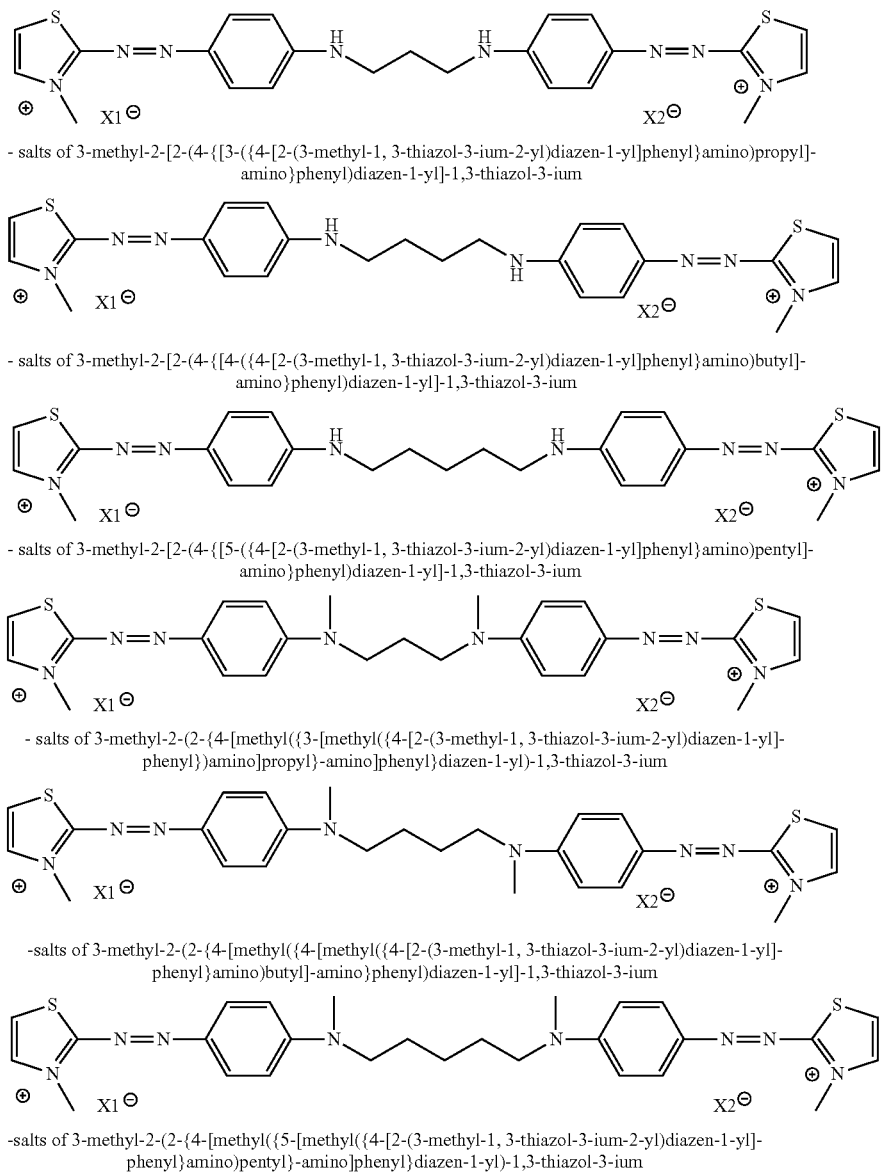

- salts of 3-methyl-2-[2-(4-{[3-({4-[2-(3-methyl-1, 3-thiazol-3-ium-2-yl)diazen-1-yl]phenyl}amino)propyl]-amino}phenyl)diazen-1-yl]-1,3-thiazol-3-ium

- salts of 3-methyl-2-[2-(4-{[4-({4-[2-(3-methyl-1, 3-thiazol-3-ium-2-yl)diazen-1-yl]phenyl}amino)butyl]-amino}phenyl)diazen-1-yl]-1,3-thiazol-3-ium

- salts of 3-methyl-2-[2-(4-{[5-({4-[2-(3-methyl-1, 3-thiazol-3-ium-2-yl)diazen-1-yl]phenyl}amino)pentyl]-amino}phenyl)diazen-1-yl]-1,3-thiazol-3-ium

- salts of 3-methyl-2-(2-{4-[methyl({3-[methyl({4-[2-(3-methyl-1, 3-thiazol-3-ium-2-yl)diazen-1-yl]-phenyl})amino]propyl}-amino]phenyl}diazen-1-yl)-1,3-thiazol-3-ium -salts of 3-methyl-2-(2-{4-[methyl({4-[methyl({4-[2-(3-methyl-1, 3-thiazol-3-ium-2-yl)diazen-1-yl]-phenyl}amino)butyl]-amino}phenyl)diazen-1-yl]-1,3-thiazol-3-ium -salts of 3-methyl-2-(2-{4-[methyl({5-[methyl({4-[2-(3-methyl-1, 3-thiazol-3-ium-2-yl)diazen-1-yl]-phenyl}amino)pentyl]-amino]phenyl}diazen-1-yl)-1,3-thiazol-3-ium

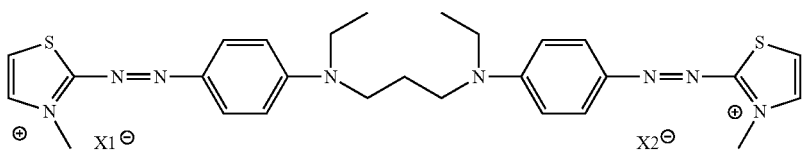

-salts of 2-(2-{4-[ethyl({3-[ethyl({4-[2-(3-methyl-1, 3-thiazol-3-ium-2-yl)diazen-1-yl]-phenyl})amino]-propyl}-amino]phenyl}diazen-1-yl)-3-methyl-1,3-thiazol-3-ium

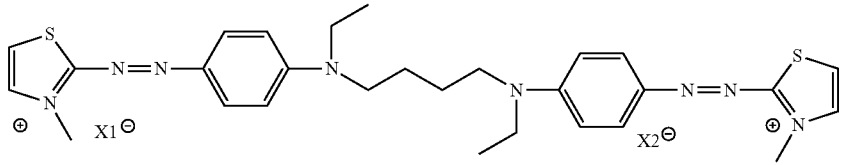

-salts of 2-(2-{4-[ethyl({4-[ethyl({4-[2-(3-methyl-1, 3-thiazol-3-ium-2-yl)diazen-1-yl]-phenyl})amino]-butyl}-amino]phenyl}diazen-1-yl)-3-methyl-1,3-thiazol-3-ium

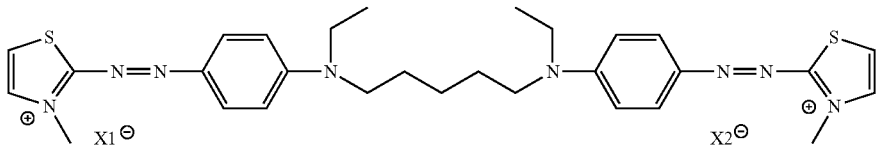

-salts of 2-(2-{4-[ethyl({5-[ethyl({4-[2-(3-methyl-1, 3-thiazol-3-ium-2-yl)diazen-1-yl]-phenyl})amino]-pentyl}-amino]phenyl}diazen-1-yl)-3-methyl-1,3-thiazol-3-ium

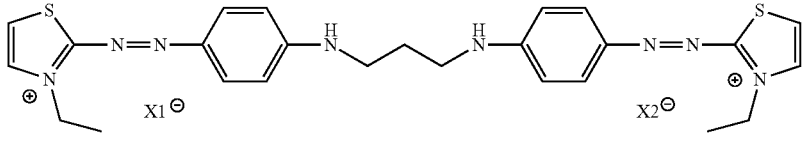

-salts of 3-ethyl-2[2-(4-{[3-({4[2-(3-ethyl-1, 3-thiazol-3-ium-2-yl)diazen-1-yl]phenyl}amino)propyl]-amino}phenyl)diazen-1-yl]-1,3-thiazol-3-ium

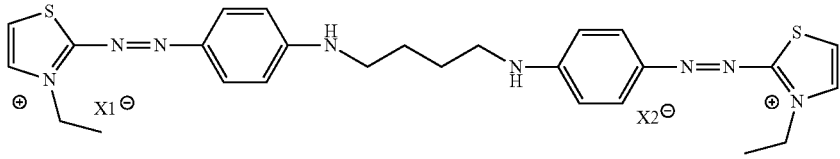

-salts of 3-ethyl-2[2-(4-{[4-({4-[2-(3-ethyl-1, 3-thiazol-3-ium-2-yl)diazen-1-yl]phenyl}amino)butyl]-amino}phenyl)diazen-1-yl]-1,3-thiazol-3-ium

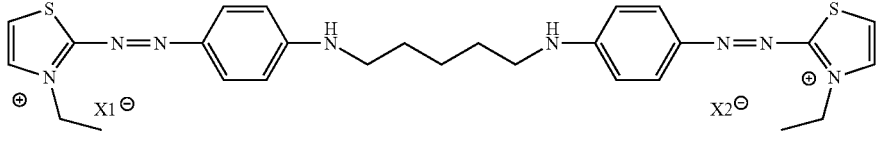

-salts of 3-ethyl-2[2-(4-{[5-({4-[2-(3-ethyl-1, 3-thiazol-3-ium-2-yl)diazen-1-yl]phenyl}amino)pentyl]-amino}phenyl)diazen-1-yl]-1,3-thiazol-3-ium

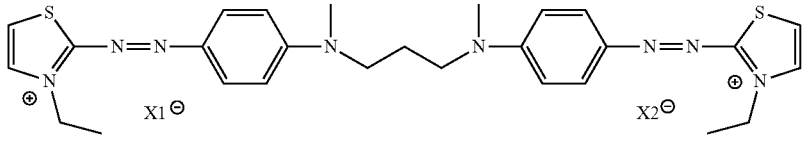

-salts of 3-ethyl-2-[2-(4-{[3-({4-[2-(3-ethyl-1, 3-thiazol-3-ium-2-yl)diazen-1-yl]phenyl}(methyl)amino)-propyl]-amino}phenyl)diazen-1-yl]-1,3-thiazol-3-ium

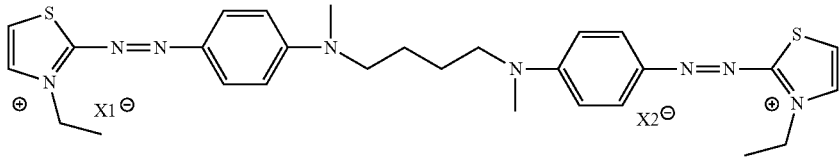

-salts of 3-ethyl-2-[2-(4-{[4-({4-[2-(3-ethyl-1, 3-thiazol-3-ium-2-yl)diazen-1-yl]phenyl}-(methyl)amino)butyl]amino}phenyl)diazen-1-yl]-1,3-thiazol-3-ium

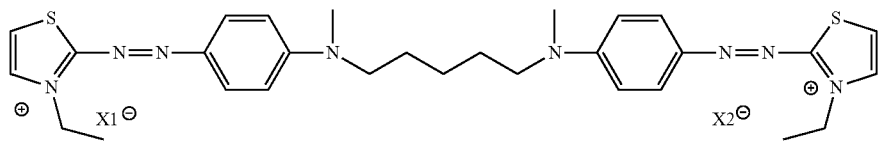

-salts of 3-ethyl-2-[2-(4-{[5-({4-[2-(3-ethyl-1, 3-thiazol-3-ium-2-yl)diazen-1-yl]phenyl}(methyl)amino)-pentyl](methyl)amino}phenyl)diazen-1-yl]-1,3-thiazol-3-ium

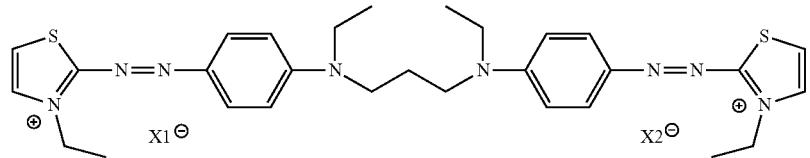

-salts of 3-ethyl-2-(2-{4-[ethyl({3-[ethyl({4-[2-(3-ethyl-1, 3-thiazol-3-ium-2-yl)diazen-1-yl]phenyl}amino]-propyl})amino]phenyl}diazen-1-yl)-1,3-thiazol-3-ium

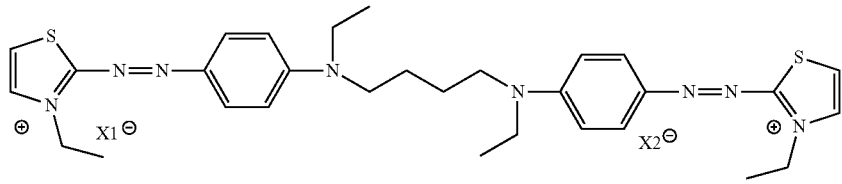

-salts of 3-ethyl-2-(2-{4-[ethyl({4-[ethyl({4-[2-(3-ethyl-1, 3-thiazol-3-ium-2-yl)diazen-1-yl]phenyl})-aminolbutyl})aminolphenyl}diazen-1-yl)-1,3-thiazol-3-ium

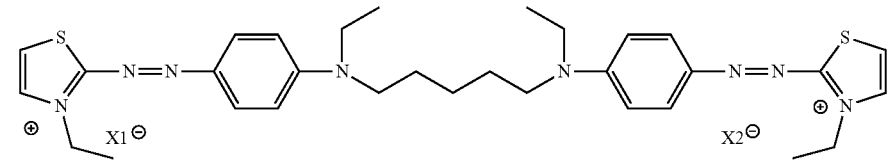

-salts of 3-ethyl-2-(2-{4-[ethyl({5-[ethyl({4-{[5-({4-[2-(3-ethyl-1, 3-thiazol-3-ium-2-yl)diazen-1-yl]phenyl})-amino]pentyl})amino]phenyl}diazen-1-yl)-1,3-thiazol-3-ium

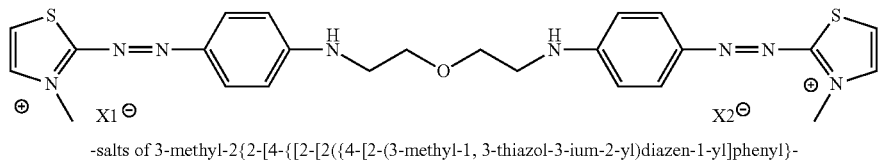

-salts of 3-methyl-2{2-[4-{[2-[2({4-[2-(3-methyl-1, 3-thiazol-3-ium-2-yl)diazen-1-yl]phenyl}-amino)ethoxy]ethyl}amino)phenyl]diazen-1-yl}-1,3-thiazol-3-ium

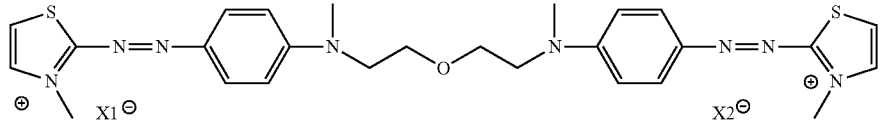

-salts of 3-methyl-2(2-{4-[methly(2-{2-[methyl({4-[2-(3-methyl-1, 3-thiazol-3-ium-2-yl)diazen-1-yl]phenyl})-amino]ethoxy}ethyl)amino]phenyl}diazen-1-yl)-1,3-thiazol-3-ium

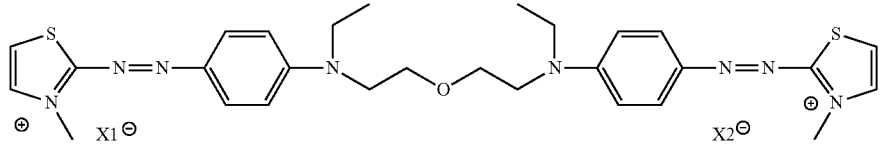

-salts of 2-(2-{4-[ethly(2-{2-[ethyl({4-[2-(3-ethyl-1, 3-thiazol-3-ium-2-yl)diazen-1-yl]phenyl})-amino]ethoxy}ethyl)amino]phenyl}diazen-1-yl)-1,3-thiazol-3-ium

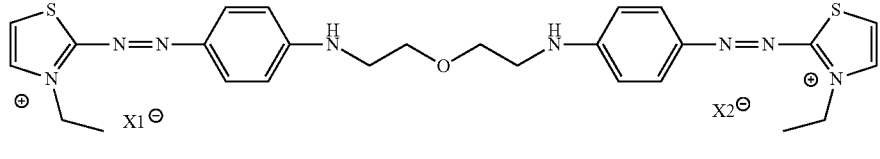

-salts of 3-ethyl-2-{2-{4-({2-[2-({4-[2-(3-ethyl-1, 3-thiazol-3-ium-2-yl)diazen-1-yl]phenyl}amino)-ethoxy]ethyl}amino)phenyl]diazen-1-yl}-1,3-thiazol-3-ium -continued

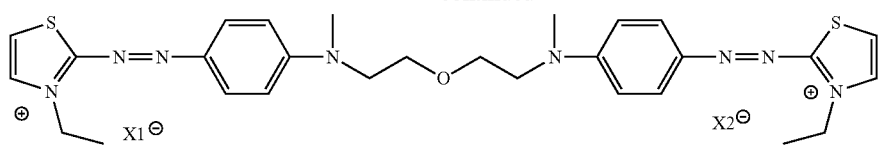

-salts of 3-ethyl-2-{2-[4-({2-[2-({4-[2-(3-ethyl-1, 3-thiazol-3-ium-2-yl)diazen-1-yl]phenyl}(methyl)amino)-ethoxy]ethyl}(methyl)amino)phenyl]diazen-1-yl}-1,3-thiazol-3-ium

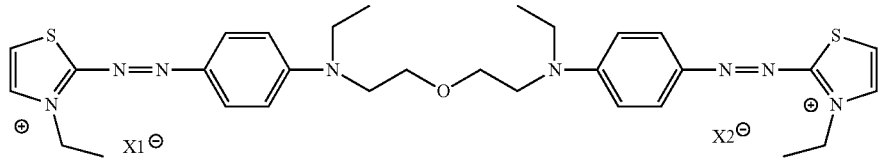

-salts of 3-ethyl-2-(2-{4-[ethyl(2-{2[ethyl({4-[2-(3-ethyl-1, 3-thiazol-3-ium-2-yl)diazen-1-yl]phenyl})-amino]ethoxy}ethyl)amino]phenyl}diazen-1-yl)-1,3-thiazol-3-ium

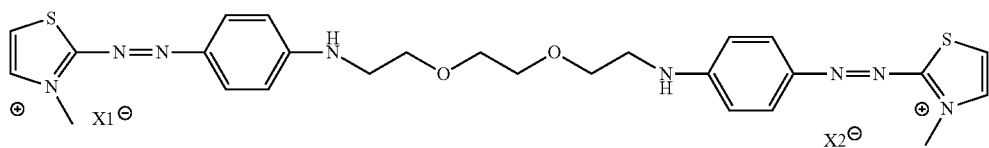

-salts of 3-methyl-2-{2-[4-(10-{4-[2-(3-methyl-1, 3-thiazol-3-ium-2-yl)diazen-1-yl]phenyl}-4,7-dioxa-1,10-diazadecan-1-yl)phenyl]diazen-1-yl}-1,3-thiazol-3-ium

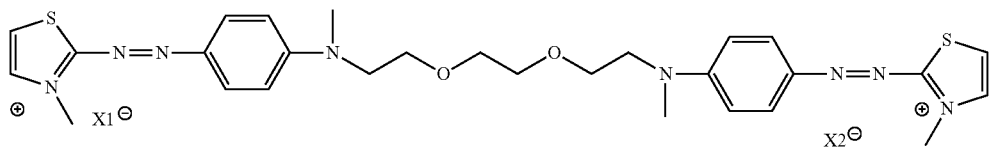

-salts of 3-methyl-2-{2-[4-(11-{4-[2-(3-methyl-1, 3-thiazol-3-ium-2-yl)diazen-1-yl]phenyl}-5,8-dioxa-2,11-diazadodecan-2-yl)phenyl]diazen-1-yl}-1,3-thiazol-3-ium

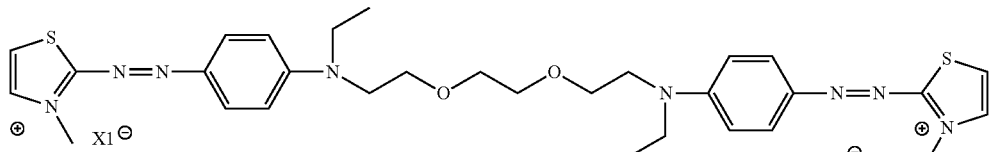

-salts of 3-methyl-2-{2-[4-(12-{4-[2-(3-methyl-1, 3-thiazol-3-ium-2-yl)diazen-1-yl]phenyl}-6,9-dioxa-3,12-diazatetradecan-2-yl)phenyl]diazen-1-yl}-1,3-thiazol-3-ium

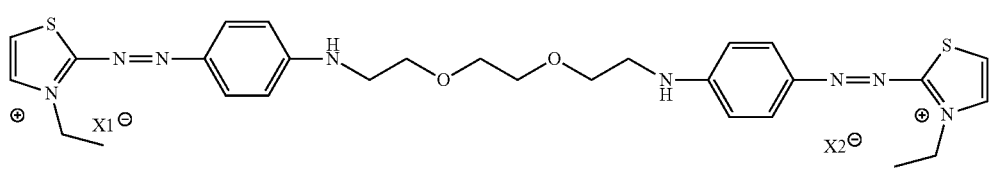

-salts of 3-ethyl-2-{2-[4-(10-{4-[2-(3-ethyl-1,3-thiazol-3-ium-2-yl)diazen-1-yl]phenyl}-4,7-dioxa-1,10-diazadecan-1-yl)phenyl]diazen-1-yl}-1,3-thiazol-3-ium

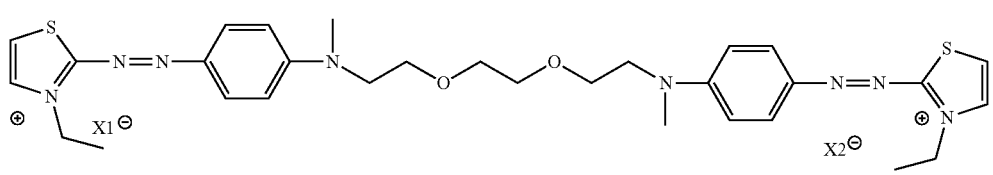

-salts of 3-ethyl-2-{2-[4-(11-{4-[2-(3-ethyl-1,3-thiazol-3-ium-2-yl)diazen-1-yl]phenyl}-5,8-dioxa-2,11-diazadecan-2-yl)phenyl]diazen-1-yl}-1,3-thiazol-3-ium

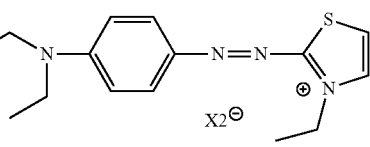

-salts of 3-ethyl-2-{2-[4-(12-{4-[2-(3-ethyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium The aforementioned compounds are dicationic dimeric dyes, the organic dication being neutralized by the two anions $X1^-$ and $X2^-$. The anions $X1^-$ and $X2^-$ can each be a physiologically acceptable anion, preferably from the group comprising chloride, bromide, iodide, methyl sulfate, methyl sulfonate, p-toluenesulfonate, acetate, hydrogen ½ sulfate, ½ sulfate, or tetrachlorozincate.

In a particularly preferred embodiment, an agent of the present disclosure for dyeing keratinic fibers is characterized in that it contains as the dye of the formula (a) at least one compound that is selected from the group comprising 3-methyl-2-[2-(4-{[3-({4-[2-(3-methyl-1,3-thiazol-3-ium-2-yl)diazen-1-yl]phenyl}amino)propyl]amino}-phenyl)diazen-1-yl]-1,3-thiazol-3-ium dichloride 3-methyl-2-[2-(4-{[3-({4-[2-(3-methyl-1,3-thiazol-3-ium-2-yl)diazen-1-yl]phenyl}amino)propyl]amino}-phenyl)diazen-1-yl]-1,3-thiazol-3-ium dibromide 3-methyl-2-[2-(4-{[3-({4-[2-(3-methyl-1,3-thiazol-3-ium-2-yl)diazen-1-yl]phenyl}amino)propyl]-amino}phenyl)diazen-1-yl]-1,3-thiazol-3-ium sulfate 3-methyl-2-[2-(4-{[3-({4-[2-(3-methyl-1,3-thiazol-3-ium-2-yl)diazen-1-yl]phenyl}amino)propyl]-amino}phenyl)diazen-1-yl]-1,3-thiazol-3-ium di(toluenesulfonate)

3-methyl-2-[2-(4-{[3-({4-[2-(3-methyl-1,3-thiazol-3-ium-2-yl)diazen-1-yl]phenyl}amino)propyl]-amino}phenyl)diazen-1-yl]-1,3-thiazol-3-ium di(methyl sulfate)

3-methyl-2-[2-(4-{[3-({4-[2-(3-methyl-1,3-thiazol-3-ium-2-yl)diazen-1-yl]phenyl}amino)propyl]amino}-phenyl)diazen-1-yl]-1,3-thiazol-3-ium tetrachlorozincate 3-methyl-2-[2-(4-{[4-({4-[2-(3-methyl-1,3-thiazol-3-ium-2-yl)diazen-1-yl]phenyl}amino)butyl]-amino}phenyl)diazen-1-yl]-1,3-thiazol-3-ium dichloride 3-methyl-2-[2-(4-{[4-({4-[2-(3-methyl-1,3-thiazol-3-ium-2-yl)diazen-1-yl]phenyl}amino)butyl]-amino}phenyl)diazen-1-yl]-1,3-thiazol-3-ium dibromide 3-methyl-2-[2-(4-{[4-({4-[2-(3-methyl-1,3-thiazol-3-ium-2-yl)diazen-1-yl]phenyl}amino)butyl]-amino}phenyl)diazen-1-yl]-1,3-thiazol-3-ium sulfate 3-methyl-2-[2-(4-{[4-({4-[2-(3-methyl-1,3-thiazol-3-ium-2-yl)diazen-1-yl]phenyl}amino)butyl]-amino}phenyl)diazen-1-yl]-1,3-thiazol-3-ium di(toluenesulfonate)

3-methyl-2-[2-(4-{[4-({4-[2-(3-methyl-1,3-thiazol-3-ium-2-yl)diazen-1-yl]phenyl}amino)butyl]-amino}phenyl)diazen-1-yl]-1,3-thiazol-3-ium di(methyl sulfate)

3-methyl-2-[2-(4-{[4-({4-[2-(3-methyl-1,3-thiazol-3-ium-2-yl)diazen-1-yl]phenyl}amino)butyl]-amino}phenyl)diazen-1-yl]-1,3-thiazol-3-ium tetrachlorozincate 3-methyl-2-[2-(4-{[5-({4-[2-(3-methyl-1,3-thiazol-3-ium-2-yl)diazen-1-yl]phenyl}amino)pentyl]-amino}phenyl)diazen-1-yl]-1,3-thiazol-3-ium dichloride 3-methyl-2-[2-(4-{[5-({4-[2-(3-methyl-1,3-thiazol-3-ium-2-yl)diazen-1-yl]phenyl}amino)pentyl]-amino}phenyl)diazen-1-yl]-1,3-thiazol-3-ium dibromide 3-methyl-2-[2-(4-{[5-({4-[2-(3-methyl-1,3-thiazol-3-ium-2-yl)diazen-1-yl]phenyl}amino)pentyl]-amino}phenyl)diazen-1-yl]-1,3-thiazol-3-ium sulfate 3-methyl-2-[2-(4-{[5-({4-[2-(3-methyl-1,3-thiazol-3-ium-2-yl)diazen-1-yl]phenyl}amino)pentyl]-amino}phenyl)diazen-1-yl]-1,3-thiazol-3-ium di(toluenesulfonate)

3-methyl-2-[2-(4-{[5-({4-[2-(3-methyl-1,3-thiazol-3-ium-2-yl)diazen-1-yl]phenyl}amino)pentyl]-amino}phenyl)diazen-1-yl]-1,3-thiazol-3-ium (di (methyl sulfate)

3-methyl-2-[2-(4-{[5-({4-[2-(3-methyl-1,3-thiazol-3-ium-2-yl)diazen-1-yl]phenyl}amino)pentyl]-amino}phenyl)diazen-1-yl]-1,3-thiazol-3-ium tetrachlorozincate 3-methyl-2-(2-{4-[methyl({3-[methyl({4-[2-(3-methyl-1,3-thiazol-3-ium-2-yl)diazen-1-yl]phenyl})-amino]propyl})amino]phenyl}diazen-1-yl)-1,3-thiazol-3-ium dichloride 3-methyl-2-(2-{4-[methyl({3-[methyl({4-[2-(3-methyl-1,3-thiazol-3-ium-2-yl)diazen-1-yl]phenyl})-amino]propyl})amino]phenyl}diazen-1-yl)-1,3-thiazol-3-ium dibromide 3-methyl-2-(2-{4-[methyl({3-[methyl({4-[2-(3-methyl-1,3-thiazol-3-ium-2-yl)diazen-1-yl]phenyl})-amino]propyl})amino]phenyl}diazen-1-yl)-1,3-thiazol-3-ium sulfate 3-methyl-2-(2-{4-[methyl({3-[methyl({4-[2-(3-methyl-1,3-thiazol-3-ium-2-yl)diazen-1-yl]phenyl})-amino]propyl})amino]phenyl}diazen-1-yl)-1,3-thiazol-3-ium di(toluenesulfonate)

3-methyl-2-(2-{4-[methyl({3-[methyl({4-[2-(3-methyl-1,3-thiazol-3-ium-2-yl)diazen-1-yl]phenyl})-amino]propyl})amino]phenyl}diazen-1-yl)-1,3-thiazol-3-ium di(methyl sulfate)

3-methyl-2-(2-{4-[methyl({3-[methyl({4-[2-(3-methyl-1,3-thiazol-3-ium-2-yl)diazen-1-yl]phenyl})-amino]propyl})amino]phenyl}diazen-1-yl)-1,3-thiazol-3-ium tetrachlorozincate 3-methyl-2-(2-{4-[methyl({4-[methyl({4-[2-(3-methyl-1,3-thiazol-3-ium-2-yl)diazen-1-yl]phenyl})-amino]butyl})amino]phenyl}diazen-1-yl)-1,3-thiazol-3-ium dichloride 3-methyl-2-(2-{4-[methyl({4-[methyl({4-[2-(3-methyl-1,3-thiazol-3-ium-2-yl)diazen-1-yl]phenyl})-amino]butyl})amino]phenyl}diazen-1-yl)-1,3-thiazol-3-ium dibromide 3-methyl-2-(2-{4-[methyl({4-[methyl({4-[2-(3-methyl-1,3-thiazol-3-ium-2-yl)diazen-1-yl]phenyl})-amino]butyl})amino]phenyl}diazen-1-yl)-1,3-thiazol-3-ium sulfate 3-methyl-2-(2-{4-[methyl({4-[methyl({4-[2-(3-methyl-1,3-thiazol-3-ium-2-yl)diazen-1-yl]phenyl})-amino]butyl})amino]phenyl}diazen-1-yl)-1,3-thiazol-3-ium di(toluenesulfonate)

3-methyl-2-(2-{4-[methyl({4-[methyl({4-[2-(3-methyl-1,3-thiazol-3-ium-2-yl)diazen-1-yl]phenyl})-amino]butyl})amino]phenyl}diazen-1-yl)-1,3-thiazol-3-ium di(methyl sulfate)

3-methyl-2-(2-{4-[methyl({4-[methyl({4-[2-(3-methyl-1,3-thiazol-3-ium-2-yl)diazen-1-yl]phenyl})-amino]butyl})amino]phenyl}diazen-1-yl)-1,3-thiazol-3-ium tetrachlorozincate 3-methyl-2-(2-{4-[methyl({5-[methyl({4-[2-(3-methyl-1,3-thiazol-3-ium-2-yl)diazen-1-yl]phenyl})-amino]pentyl})amino]phenyl}diazen-1-yl)-1,3-thiazol-3-ium dichloride 3-methyl-2-(2-{4-[methyl({5-[methyl({4-[2-(3-methyl-1,3-thiazol-3-ium-2-yl)diazen-1-yl]phenyl})-amino]pentyl})amino]phenyl}diazen-1-yl)-1,3-thiazol-3-ium dibromide 3-methyl-2-(2-{4-[methyl({5-[methyl({4-[2-(3-methyl-1,3-thiazol-3-ium-2-yl)diazen-1-yl]phenyl})-amino]pentyl})amino]phenyl}diazen-1-yl)-1,3-thiazol-3-ium sulfate 3-methyl-2-(2-{4-[methyl({5-[methyl({4-[2-(3-methyl-1,3-thiazol-3-ium-2-yl)diazen-1-yl]phenyl})-amino]pentyl})amino]phenyl}diazen-1-yl)-1,3-thiazol-3-ium di(toluenesulfonate)

3-methyl-2-(2-{4-[methyl({5-[methyl({4-[2-(3-methyl-1,3-thiazol-3-ium-2-yl)diazen-1-yl]phenyl})-amino]pentyl})amino]phenyl}diazen-1-yl)-1,3-thiazol-3-ium di(methyl sulfate)

3-methyl-2-(2-{4-[methyl({5-[methyl({4-[2-(3-methyl-1,3-thiazol-3-ium-2-yl)diazen-1-yl]phenyl})-amino]pentyl})amino]phenyl}diazen-1-yl)-1,3-thiazol-3-ium tetrachlorozincate 2-(2-{4-[ethyl({3-[ethyl({4-[2-(3-methyl-1,3-thiazol-3-ium-2-yl)diazen-1-yl]phenyl})amino]propyl})-amino]phenyl}diazen-1-yl)-3-methyl-1,3-thiazol-3-ium dichloride 2-(2-{4-[ethyl({3-[ethyl({4-[2-(3-methyl-1,3-thiazol-3-ium-2-yl)diazen-1-yl]phenyl})amino]propyl})-amino]phenyl}diazen-1-yl)-3-methyl-1,3-thiazol-3-ium dibromide 2-(2-{4-[ethyl({3-[ethyl({4-[2-(3-methyl-1,3-thiazol-3-ium-2-yl)diazen-1-yl]phenyl})amino]propyl})-amino]phenyl}diazen-1-yl)-3-methyl-1,3-thiazol-3-ium sulfate 2-(2-{4-[ethyl({3-[ethyl({4-[2-(3-methyl-1,3-thiazol-3-ium-2-yl)diazen-1-yl]phenyl})amino]propyl})-amino]phenyl}diazen-1-yl)-3-methyl-1,3-thiazol-3-ium di(toluenesulfonate)

2-(2-{4-[ethyl({3-[ethyl({4-[2-(3-methyl-1,3-thiazol-3-ium-2-yl)diazen-1-yl]phenyl})amino]propyl})-amino]phenyl}diazen-1-yl)-3-methyl-1,3-thiazol-3-ium di(methyl sulfate)

2-(2-{4-[ethyl({3-[ethyl({4-[2-(3-methyl-1,3-thiazol-3-ium-2-yl)diazen-1-yl]phenyl})amino]propyl})-amino]phenyl}diazen-1-yl)-3-methyl-1,3-thiazol-3-ium tetrachlorozincate 2-(2-{4-[ethyl({4-[ethyl({4-[2-(3-methyl-1,3-thiazol-3-ium-2-yl)diazen-1-yl]phenyl})amino]butyl})-amino]phenyl}diazen-1-yl)-3-methyl-1,3-thiazol-3-ium dichloride 2-(2-{4-[ethyl({4-[ethyl({4-[2-(3-methyl-1,3-thiazol-3-ium-2-yl)diazen-1-yl]phenyl})amino]butyl})-amino]phenyl}diazen-1-yl)-3-methyl-1,3-thiazol-3-ium dibromide 2-(2-{4-[ethyl({4-[ethyl({4-[2-(3-methyl-1,3-thiazol-3-ium-2-yl)diazen-1-yl]phenyl})amino]butyl})-amino]phenyl}diazen-1-yl)-3-methyl-1,3-thiazol-3-ium sulfate 2-(2-{4-[ethyl({4-[ethyl({4-[2-(3-methyl-1,3-thiazol-3-ium-2-yl)diazen-1-yl]phenyl})amino]butyl})-amino]phenyl}diazen-1-yl)-3-methyl-1,3-thiazol-3-ium di(toluenesulfonate)

2-(2-{4-[ethyl({4-[ethyl({4-[2-(3-methyl-1,3-thiazol-3-ium-2-yl)diazen-1-yl]phenyl})amino]butyl})-amino]phenyl}diazen-1-yl)-3-methyl-1,3-thiazol-3-ium di(methyl sulfate)

2-(2-{4-[ethyl({4-[ethyl({4-[2-(3-methyl-1,3-thiazol-3-ium-2-yl)diazen-1-yl]phenyl})amino]butyl})-amino]phenyl}diazen-1-yl)-3-methyl-1,3-thiazol-3-ium tetrachlorozincate 2-(2-{4-[ethyl({5-[ethyl({4-[2-(3-methyl-1,3-thiazol-3-ium-2-yl)diazen-1-yl]phenyl})amino]pentyl})-amino]phenyl}diazen-1-yl)-3-methyl-1,3-thiazol-3-ium dichloride 2-(2-{4-[ethyl({5-[ethyl({4-[2-(3-methyl-1,3-thiazol-3-ium-2-yl)diazen-1-yl]phenyl})amino]pentyl})-amino]phenyl}diazen-1-yl)-3-methyl-1,3-thiazol-3-ium dibromide 2-(2-{4-[ethyl({5-[ethyl({4-[2-(3-methyl-1,3-thiazol-3-ium-2-yl)diazen-1-yl]phenyl})amino]pentyl})-amino]phenyl}diazen-1-yl)-3-methyl-1,3-thiazol-3-ium sulfate 2-(2-{4-[ethyl({5-[ethyl({4-[2-(3-methyl-1,3-thiazol-3-ium-2-yl)diazen-1-yl]phenyl})amino]pentyl})-amino]phenyl}diazen-1-yl)-3-methyl-1,3-thiazol-3-ium di(toluenesulfonate)

2-(2-{4-[ethyl({5-[ethyl({4-[2-(3-methyl-1,3-thiazol-3-ium-2-yl)diazen-1-yl]phenyl})amino]pentyl})-amino]phenyl}diazen-1-yl)-3-methyl-1,3-thiazol-3-ium di(methyl sulfate)

2-(2-{4-[ethyl({5-[ethyl({4-[2-(3-methyl-1,3-thiazol-3-ium-2-yl)diazen-1-yl]phenyl})amino]pentyl})-amino]phenyl}diazen-1-yl)-3-methyl-1,3-thiazol-3-ium tetrachlorozincate 3-ethyl-2-[2-(4-{[3-({4-[2-(3-ethyl-1,3-thiazol-3-ium-2-yl)diazen-1-yl]phenyl}amino)propyl]amino}-phenyl)diazen-1-yl]-1,3-thiazol-3-ium dichloride 3-ethyl-2-[2-(4-{[3-({4-[2-(3-ethyl-1,3-thiazol-3-ium-2-yl)diazen-1-yl]phenyl}amino)propyl]amino}-phenyl)diazen-1-yl]-1,3-thiazol-3-ium dibromide 3-ethyl-2-[2-(4-{[3-({4-[2-(3-ethyl-1,3-thiazol-3-ium-2-yl)diazen-1-yl]phenyl}amino)propyl]amino}-phenyl)diazen-1-yl]-1,3-thiazol-3-ium sulfate 3-ethyl-2-[2-(4-{[3-({4-[2-(3-ethyl-1,3-thiazol-3-ium-2-yl)diazen-1-yl]phenyl}amino)propyl]amino}-phenyl)diazen-1-yl]-1,3-thiazol-3-ium di(toluenesulfonate)

3-ethyl-2-[2-(4-{[3-({4-[2-(3-ethyl-1,3-thiazol-3-ium-2-yl)diazen-1-yl]phenyl}amino)propyl]amino}-phenyl)diazen-1-yl]-1,3-thiazol-3-ium di(methyl sulfate)

3-ethyl-2-[2-(4-{[3-({4-[2-(3-ethyl-1,3-thiazol-3-ium-2-yl)diazen-1-yl]phenyl}amino)propyl]amino}-phenyl)diazen-1-yl]-1,3-thiazol-3-ium tetrachlorozincate 3-ethyl-2-[2-(4-{[4-({4-[2-(3-ethyl-1,3-thiazol-3-ium-2-yl)diazen-1-yl]phenyl}amino)butyl]amino}-phenyl)diazen-1-yl]-1,3-thiazol-3-ium dichloride
3-ethyl-2-[2-(4-{[4-({4-[2-(3-ethyl-1,3-thiazol-3-ium-2-yl)diazen-1-yl]phenyl}amino)butyl]amino}-phenyl)diazen-1-yl]-1,3-thiazol-3-ium dibromide
3-ethyl-2-[2-(4-{[4-({4-[2-(3-ethyl-1,3-thiazol-3-ium-2-yl)diazen-1-yl]phenyl}amino)butyl]amino}-phenyl)diazen-1-yl]-1,3-thiazol-3-ium sulfate
3-ethyl-2-[2-(4-{[4-({4-[2-(3-ethyl-1,3-thiazol-3-ium-2-yl)diazen-1-yl]phenyl}amino)butyl]amino}-phenyl)diazen-1-yl]-1,3-thiazol-3-ium di(toluenesulfonate)
3-ethyl-2-[2-(4-{[4-({4-[2-(3-ethyl-1,3-thiazol-3-ium-2-yl)diazen-1-yl]phenyl}amino)butyl]amino}-phenyl)diazen-1-yl]-1,3-thiazol-3-ium di(methyl sulfate)
3-ethyl-2-[2-(4-{[4-({4-[2-(3-ethyl-1,3-thiazol-3-ium-2-yl)diazen-1-yl]phenyl}amino)butyl]amino}-phenyl)diazen-1-yl]-1,3-thiazol-3-ium tetrachlorozincate
3-ethyl-2-[2-(4-{[5-({4-[2-(3-ethyl-1,3-thiazol-3-ium-2-yl)diazen-1-yl]phenyl}amino)pentyl]amino}-phenyl)diazen-1-yl]-1,3-thiazol-3-ium dichloride
3-ethyl-2-[2-(4-{[5-({4-[2-(3-ethyl-1,3-thiazol-3-ium-2-yl)diazen-1-yl]phenyl}amino)pentyl]amino}-phenyl)diazen-1-yl]-1,3-thiazol-3-ium dibromide
3-ethyl-2-[2-(4-{[5-({4-[2-(3-ethyl-1,3-thiazol-3-ium-2-yl)diazen-1-yl]phenyl}amino)pentyl]amino}-phenyl)diazen-1-yl]-1,3-thiazol-3-ium sulfate
3-ethyl-2-[2-(4-{[5-({4-[2-(3-ethyl-1,3-thiazol-3-ium-2-yl)diazen-1-yl]phenyl}amino)pentyl]amino}-phenyl)diazen-1-yl]-1,3-thiazol-3-ium di(toluenesulfonate)
3-ethyl-2-[2-(4-{[5-({4-[2-(3-ethyl-1,3-thiazol-3-ium-2-yl)diazen-1-yl]phenyl}amino)pentyl]amino}-phenyl)diazen-1-yl]-1,3-thiazol-3-ium di(methyl sulfate)
3-ethyl-2-[2-(4-{[5-({4-[2-(3-ethyl-1,3-thiazol-3-ium-2-yl)diazen-1-yl]phenyl}amino)pentyl]amino}-phenyl)diazen-1-yl]-1,3-thiazol-3-ium tetrachlorozincate
3-ethyl-2-[2-(4-{[3-({4-[2-(3-ethyl-1,3-thiazol-3-ium-2-yl)diazen-1-yl]phenyl}(methyl)amino)propyl]-(methyl)amino}phenyl)diazen-1-yl]-1,3-thiazol-3-ium dichloride
3-ethyl-2-[2-(4-{[3-({4-[2-(3-ethyl-1,3-thiazol-3-ium-2-yl)diazen-1-yl]phenyl}(methyl)amino)propyl]-(methyl)amino}phenyl)diazen-1-yl]-1,3-thiazol-3-ium dibromide
3-ethyl-2-[2-(4-{[3-({4-[2-(3-ethyl-1,3-thiazol-3-ium-2-yl)diazen-1-yl]phenyl}(methyl)amino)propyl]-(methyl)amino}phenyl)diazen-1-yl]-1,3-thiazol-3-ium sulfate
3-ethyl-2-[2-(4-{[3-({4-[2-(3-ethyl-1,3-thiazol-3-ium-2-yl)diazen-1-yl]phenyl}(methyl)amino)propyl]-(methyl)amino}phenyl)diazen-1-yl]-1,3-thiazol-3-ium di(toluenesulfonate)
3-ethyl-2-[2-(4-{[3-({4-[2-(3-ethyl-1,3-thiazol-3-ium-2-yl)diazen-1-yl]phenyl}-(methyl)amino)propyl]-(methyl)amino}phenyl)diazen-1-yl]-1,3-thiazol-3-ium di(methyl sulfate)
3-ethyl-2-[2-(4-{[3-({4-[2-(3-ethyl-1,3-thiazol-3-ium-2-yl)diazen-1-yl]phenyl}-(methyl)amino)propyl]-(methyl)amino}phenyl)diazen-1-yl]-1,3-thiazol-3-ium tetrachlorozincate
3-ethyl-2-[2-(4-{[4-({4-[2-(3-ethyl-1,3-thiazol-3-ium-2-yl)diazen-1-yl]phenyl}(methyl)amino)butyl]-(methyl)amino}phenyl)diazen-1-yl]-1,3-thiazol-3-ium dichloride
3-ethyl-2-[2-(4-{[4-({4-[2-(3-ethyl-1,3-thiazol-3-ium-2-yl)diazen-1-yl]phenyl}(methyl)amino)butyl]-(methyl)amino}phenyl)diazen-1-yl]-1,3-thiazol-3-ium dibromide
3-ethyl-2-[2-(4-{[4-({4-[2-(3-ethyl-1,3-thiazol-3-ium-2-yl)diazen-1-yl]phenyl}(methyl)amino)butyl]-(methyl)amino}phenyl)diazen-1-yl]-1,3-thiazol-3-ium sulfate
3-ethyl-2-[2-(4-{[4-({4-[2-(3-ethyl-1,3-thiazol-3-ium-2-yl)diazen-1-yl]phenyl}-(methyl)amino)butyl]-(methyl)amino}phenyl)diazen-1-yl]-1,3-thiazol-3-ium di(toluenesulfonate)
3-ethyl-2-[2-(4-{[4-({4-[2-(3-ethyl-1,3-thiazol-3-ium-2-yl)diazen-1-yl]phenyl}-(methyl)amino)butyl]-(methyl)amino}phenyl)diazen-1-yl]-1,3-thiazol-3-ium di(methyl sulfate)
3-ethyl-2-[2-(4-{[4-({4-[2-(3-ethyl-1,3-thiazol-3-ium-2-yl)diazen-1-yl]phenyl}-(methyl)amino)butyl]-(methyl)amino}phenyl)diazen-1-yl]-1,3-thiazol-3-ium
3-ethyl-2-[2-(4-{[5-({4-[2-(3-ethyl-1,3-thiazol-3-ium-2-yl)diazen-1-yl]phenyl}(methyl)amino)pentyl]-(methyl)amino}phenyl)diazen-1-yl]-1,3-thiazol-3-ium dichloride
3-ethyl-2-[2-(4-{[5-({4-[2-(3-ethyl-1,3-thiazol-3-ium-2-yl)diazen-1-yl]phenyl}(methyl)amino)pentyl]-(methyl)amino}phenyl)diazen-1-yl]-1,3-thiazol-3-ium dibromide
3-ethyl-2-[2-(4-{[5-({4-[2-(3-ethyl-1,3-thiazol-3-ium-2-yl)diazen-1-yl]phenyl}(methyl)amino)pentyl]-(methyl)amino}phenyl)diazen-1-yl]-1,3-thiazol-3-ium sulfate
3-ethyl-2-[2-(4-{[5-({4-[2-(3-ethyl-1,3-thiazol-3-ium-2-yl)diazen-1-yl]phenyl}-(methyl)amino)pentyl]-(methyl)amino}phenyl)diazen-1-yl]-1,3-thiazol-3-ium di(toluenesulfonate)
3-ethyl-2-[2-(4-{[5-({4-[2-(3-ethyl-1,3-thiazol-3-ium-2-yl)diazen-1-yl]phenyl}-(methyl)amino)pentyl]-(methyl)amino}phenyl)diazen-1-yl]-1,3-thiazol-3-ium di(methyl sulfate)
3-ethyl-2-[2-(4-{[5-({4-[2-(3-ethyl-1,3-thiazol-3-ium-2-yl)diazen-1-yl]phenyl}-(methyl)amino)pentyl]-(methyl)amino}phenyl)diazen-1-yl]-1,3-thiazol-3-ium tetrachlorozincate
3-ethyl-2-(2-{4-[ethyl({3-[ethyl({4-[2-(3-ethyl-1,3-thiazol-3-ium-2-yl)diazen-1-yl]phenyl})amino]-propyl})amino]phenyl}diazen-1-yl)-1,3-thiazol-3-ium dichloride
3-ethyl-2-(2-{4-[ethyl({3-[ethyl({4-[2-(3-ethyl-1,3-thiazol-3-ium-2-yl)diazen-1-yl]phenyl})amino]-propyl})amino]phenyl}diazen-1-yl)-1,3-thiazol-3-ium dibromide
3-ethyl-2-(2-{4-[ethyl({3-[ethyl({4-[2-(3-ethyl-1,3-thiazol-3-ium-2-yl)diazen-1-yl]phenyl})amino]-propyl})amino]phenyl}diazen-1-yl)-1,3-thiazol-3-ium sulfate
3-ethyl-2-(2-{4-[ethyl({3-[ethyl({4-[2-(3-ethyl-1,3-thiazol-3-ium-2-yl)diazen-1-yl]phenyl})amino]-propyl})amino]phenyl}diazen-1-yl)-1,3-thiazol-3-ium di(toluenesulfonate)
3-ethyl-2-(2-{4-[ethyl({3-[ethyl({4-[2-(3-ethyl-1,3-thiazol-3-ium-2-yl)diazen-1-yl]phenyl})amino]-propyl})amino]phenyl}diazen-1-yl)-1,3-thiazol-3-ium di(methyl sulfate)
3-ethyl-2-(2-{4-[ethyl({3-[ethyl({4-[2-(3-ethyl-1,3-thiazol-3-ium-2-yl)diazen-1-yl]phenyl})amino]-propyl})amino]phenyl}diazen-1-yl)-1,3-thiazol-3-ium tetrachlorozincate 3-ethyl-2-(2-{4-[ethyl({4-[ethyl({4-[2-(3-ethyl-1,3-thiazol-3-ium-2-yl)diazen-1-yl]phenyl})amino]-butyl})amino]phenyl}diazen-1-yl)-1,3-thiazol-3-ium dichloride 3-ethyl-2-(2-{4-[ethyl({4-[ethyl({4-[2-(3-ethyl-1,3-thiazol-3-ium-2-yl)diazen-1-yl]phenyl})amino]-butyl})amino]phenyl}diazen-1-yl)-1,3-thiazol-3-ium dibromide 3-ethyl-2-(2-{4-[ethyl({4-[ethyl({4-[2-(3-ethyl-1,3-thiazol-3-ium-2-yl)diazen-1-yl]phenyl})amino]-butyl})amino]phenyl}diazen-1-yl)-1,3-thiazol-3-ium sulfate 3-ethyl-2-(2-{4-[ethyl({4-[ethyl({4-[2-(3-ethyl-1,3-thiazol-3-ium-2-yl)diazen-1-yl]phenyl})amino]-butyl})amino]phenyl}diazen-1-yl)-1,3-thiazol-3-ium di(toluenesulfonate)

3-ethyl-2-(2-{4-[ethyl({4-[ethyl({4-[2-(3-ethyl-1,3-thiazol-3-ium-2-yl)diazen-1-yl]phenyl})amino]-butyl})amino]phenyl}diazen-1-yl)-1,3-thiazol-3-ium di(methyl sulfate)

3-ethyl-2-(2-{4-[ethyl({4-[ethyl({4-[2-(3-ethyl-1,3-thiazol-3-ium-2-yl)diazen-1-yl]phenyl})amino]-butyl})amino]phenyl}diazen-1-yl)-1,3-thiazol-3-ium tetrachlorozincate 3-ethyl-2-(2-{4-[ethyl({5-[ethyl({4-[2-(3-ethyl-1,3-thiazol-3-ium-2-yl)diazen-1-yl]phenyl})amino]-pentyl})amino]phenyl}diazen-1-yl)-1,3-thiazol-3-ium dichloride 3-ethyl-2-(2-{4-[ethyl({5-[ethyl({4-[2-(3-ethyl-1,3-thiazol-3-ium-2-yl)diazen-1-yl]phenyl})amino]-pentyl})amino]phenyl}diazen-1-yl)-1,3-thiazol-3-ium dibromide 3-ethyl-2-(2-{4-[ethyl({5-[ethyl({4-[2-(3-ethyl-1,3-thiazol-3-ium-2-yl)diazen-1-yl]phenyl})amino]-pentyl})amino]phenyl}diazen-1-yl)-1,3-thiazol-3-ium sulfate 3-ethyl-2-(2-{4-[ethyl({5-[ethyl({4-[2-(3-ethyl-1,3-thiazol-3-ium-2-yl)diazen-1-yl]phenyl})amino]-pentyl})amino]phenyl}diazen-1-yl)-1,3-thiazol-3-ium di(toluenesulfonate)

3-ethyl-2-(2-{4-[ethyl({5-[ethyl({4-[2-(3-ethyl-1,3-thiazol-3-ium-2-yl)diazen-1-yl]phenyl})amino]-pentyl})amino]phenyl}diazen-1-yl)-1,3-thiazol-3-ium di(methyl sulfate)

3-ethyl-2-(2-{4-[ethyl({5-[ethyl({4-[2-(3-ethyl-1,3-thiazol-3-ium-2-yl)diazen-1-yl]phenyl})amino]-pentyl})amino]phenyl}diazen-1-yl)-1,3-thiazol-3-ium tetrachlorozincate 3-methyl-2-{2-[4-({2-[2-({4-[2-(3-methyl-1,3-thiazol-3-ium-2-yl)diazen-1-yl]phenyl}amino)ethoxy]-ethyl}amino)phenyl]diazen-1-yl}-1,3-thiazol-3-ium dichloride 3-methyl-2-{2-[4-({2-[2-({4-[2-(3-methyl-1,3-thiazol-3-ium-2-yl)diazen-1-yl]phenyl}amino)ethoxy]-ethyl}amino)phenyl]diazen-1-yl}-1,3-thiazol-3-ium dibromide 3-methyl-2-{2-[4-({2-[2-({4-[2-(3-methyl-1,3-thiazol-3-ium-2-yl)diazen-1-yl]phenyl}amino)ethoxy]-ethyl}amino)phenyl]diazen-1-yl}-1,3-thiazol-3-ium sulfate 3-methyl-2-{2-[4-({2-[2-({4-[2-(3-methyl-1,3-thiazol-3-ium-2-yl)diazen-1-yl]phenyl}amino)ethoxy]-ethyl}amino)phenyl]diazen-1-yl}-1,3-thiazol-3-ium di(toluenesulfonate)

3-methyl-2-{2-[4-({2-[2-({4-[2-(3-methyl-1,3-thiazol-3-ium-2-yl)diazen-1-yl]phenyl}amino)ethoxy]-ethyl}amino)phenyl]diazen-1-yl}-1,3-thiazol-3-ium di(methyl sulfate)

3-methyl-2-{2-[4-({2-[2-({4-[2-(3-methyl-1,3-thiazol-3-ium-2-yl)diazen-1-yl]phenyl}amino)ethoxy]-ethyl}amino)phenyl]diazen-1-yl}-1,3-thiazol-3-ium tetrachlorozincate 3-methyl-2-(2-{4-[methyl(2-{2-[methyl({4-[2-(3-methyl-1,3-thiazol-3-ium-2-yl)diazen-1-yl]phenyl})-amino]ethoxy}ethyl)amino]phenyl}diazen-1-yl)-1,3-thiazol-3-ium dichloride 3-methyl-2-(2-{4-[methyl(2-{2-[methyl({4-[2-(3-methyl-1,3-thiazol-3-ium-2-yl)diazen-1-yl]phenyl})-amino]ethoxy}ethyl)amino]phenyl}diazen-1-yl)-1,3-thiazol-3-ium dibromide 3-methyl-2-(2-{4-[methyl(2-{2-[methyl({4-[2-(3-methyl-1,3-thiazol-3-ium-2-yl)diazen-1-yl]phenyl})-amino]ethoxy}ethyl)amino]phenyl}diazen-1-yl)-1,3-thiazol-3-ium sulfate 3-methyl-2-(2-{4-[methyl(2-{2-[methyl({4-[2-(3-methyl-1,3-thiazol-3-ium-2-yl)diazen-1-yl]phenyl})-amino]ethoxy}ethyl)amino]phenyl}diazen-1-yl)-1,3-thiazol-3-ium di(toluenesulfonate)

3-methyl-2-(2-{4-[methyl(2-{2-[methyl({4-[2-(3-methyl-1,3-thiazol-3-ium-2-yl)diazen-1-yl]phenyl})-amino]ethoxy}ethyl)amino]phenyl}diazen-1-yl)-1,3-thiazol-3-ium di(methyl sulfate)

3-methyl-2-(2-{4-[methyl(2-{2-[methyl({4-[2-(3-methyl-1,3-thiazol-3-ium-2-yl)diazen-1-yl]phenyl})-amino]ethoxy}ethyl)amino]phenyl}diazen-1-yl)-1,3-thiazol-3-ium tetrachlorozincate 2-(2-{4-[ethyl(2-{2-[ethyl({4-[2-(3-methyl-1,3-thiazol-3-ium-2-yl)diazen-1-yl]phenyl})amino]ethoxy}-ethyl)amino]phenyl}diazen-1-yl)-3-methyl-1,3-thiazol-3-ium dichloride 2-(2-{4-[ethyl(2-{2-[ethyl({4-[2-(3-methyl-1,3-thiazol-3-ium-2-yl)diazen-1-yl]phenyl})amino]ethoxy}-ethyl)amino]phenyl}diazen-1-yl)-3-methyl-1,3-thiazol-3-ium dibromide 2-(2-{4-[ethyl(2-{2-[ethyl({4-[2-(3-methyl-1,3-thiazol-3-ium-2-yl)diazen-1-yl]phenyl})amino]ethoxy}-ethyl)amino]phenyl}diazen-1-yl)-3-methyl-1,3-thiazol-3-ium sulfate 2-(2-{4-[ethyl(2-{2-[ethyl({4-[2-(3-methyl-1,3-thiazol-3-ium-2-yl)diazen-1-yl]phenyl})amino]ethoxy}-ethyl)amino]phenyl}diazen-1-yl)-3-methyl-1,3-thiazol-3-ium di(toluenesulfonate)

2-(2-{4-[ethyl(2-{2-[ethyl({4-[2-(3-methyl-1,3-thiazol-3-ium-2-yl)diazen-1-yl]phenyl})amino]-ethoxy}-ethyl)amino]phenyl}diazen-1-yl)-3-methyl-1,3-thiazol-3-ium di(methyl sulfate)

2-(2-{4-[ethyl(2-{2-[ethyl({4-[2-(3-methyl-1,3-thiazol-3-ium-2-yl)diazen-1-yl]phenyl})amino]-ethoxy}-ethyl)amino]phenyl}diazen-1-yl)-3-methyl-1,3-thiazol-3-ium tetrachlorozincate 3-ethyl-2-{2-[4-({2-[2-({4-[2-(3-ethyl-1,3-thiazol-3-ium-2-yl)diazen-1-yl]phenyl}amino)ethoxy]ethyl}-amino)phenyl]diazen-1-yl}-1,3-thiazol-3-ium dichloride 3-ethyl-2-{2-[4-({2-[2-({4-[2-(3-ethyl-1,3-thiazol-3-ium-2-yl)diazen-1-yl]phenyl}amino)ethoxy]ethyl}-amino)phenyl]diazen-1-yl}-1,3-thiazol-3-ium dibromide 3-ethyl-2-{2-[4-({2-[2-({4-[2-(3-ethyl-1,3-thiazol-3-ium-2-yl)diazen-1-yl]phenyl}amino)ethoxy]ethyl}-amino)phenyl]diazen-1-yl}-1,3-thiazol-3-ium sulfate 3-ethyl-2-{2-[4-({2-[2-({4-[2-(3-ethyl-1,3-thiazol-3-ium-2-yl)diazen-1-yl]phenyl}amino)ethoxy]ethyl}-amino)phenyl]diazen-1-yl}-1,3-thiazol-3-ium di(toluenesulfonate)

3-ethyl-2-{2-[4-({2-[2-({4-[2-(3-ethyl-1,3-thiazol-3-ium-2-yl)diazen-1-yl]phenyl}amino)ethoxy]ethyl}-amino)phenyl]diazen-1-yl}-1,3-thiazol-3-ium di(methyl sulfate)

3-ethyl-2-{2-[4-({2-[2-({4-[2-(3-ethyl-1,3-thiazol-3-ium-2-yl)diazen-1-yl]phenyl}amino)ethoxy]ethyl}-amino)phenyl]diazen-1-yl}-1,3-thiazol-3-ium tetrachlorozincate 3-ethyl-2-{2-[4-({2-[2-({4-[2-(3-ethyl-1,3-thiazol-3-ium-2-yl)diazen-1-yl]phenyl}(methyl)amino)ethoxy]-ethyl}(methyl)amino)phenyl]diazen-1-yl}-1,3-thiazol-3-ium dichloride 3-ethyl-2-{2-[4-({2-[2-({4-[2-(3-ethyl-1,3-thiazol-3-ium-2-yl)diazen-1-yl]phenyl}(methyl)amino)-ethoxy]-ethyl}(methyl)amino)phenyl]diazen-1-yl}-1,3-thiazol-3-ium dibromide 3-ethyl-2-{2-[4-({2-[2-({4-[2-(3-ethyl-1,3-thiazol-3-ium-2-yl)diazen-1-yl]phenyl}(methyl)amino)-ethoxy]ethyl}(methyl)amino)phenyl]diazen-1-yl}-1,3-thiazol-3-ium sulfate 3-ethyl-2-{2-[4-({2-[2-({4-[2-(3-ethyl-1,3-thiazol-3-ium-2-yl)diazen-1-yl]phenyl}(methyl)amino)-ethoxy]ethyl}(methyl)amino)phenyl]diazen-1-yl}-1,3-thiazol-3-ium di(toluenesulfonate)

3-ethyl-2-{2-[4-({2-[2-({4-[2-(3-ethyl-1,3-thiazol-3-ium-2-yl)diazen-1-yl]phenyl}(methyl)amino)-ethoxy]ethyl}(methyl)amino)phenyl]diazen-1-yl}-1,3-thiazol-3-ium di(methyl sulfate)

3-ethyl-2-{2-[4-({2-[2-({4-[2-(3-ethyl-1,3-thiazol-3-ium-2-yl)diazen-1-yl]phenyl}(methyl)amino)-ethoxy]-ethyl}(methyl)amino)phenyl]diazen-1-yl}-1,3-thiazol-3-ium tetrachlorozincate 3-ethyl-2-(2-{4-[ethyl(2-{2-[ethyl({4-[2-(3-ethyl-1,3-thiazol-3-ium-2-yl)diazen-1-yl]phenyl})amino]-ethoxy}ethyl)amino]phenyl}diazen-1-yl)-1,3-thiazol-3-ium dichloride 3-ethyl-2-(2-{4-[ethyl(2-{2-[ethyl({4-[2-(3-ethyl-1,3-thiazol-3-ium-2-yl)diazen-1-yl]phenyl})amino]-ethoxy}ethyl)amino]phenyl}diazen-1-yl)-1,3-thiazol-3-ium dibromide 3-ethyl-2-(2-{4-[ethyl(2-{2-[ethyl({4-[2-(3-ethyl-1,3-thiazol-3-ium-2-yl)diazen-1-yl]phenyl})amino]-ethoxy}ethyl)amino]phenyl}diazen-1-yl)-1,3-thiazol-3-ium sulfate 3-ethyl-2-(2-{4-[ethyl(2-{2-[ethyl({4-[2-(3-ethyl-1,3-thiazol-3-ium-2-yl)diazen-1-yl]phenyl})amino]-ethoxy}ethyl)amino]phenyl}diazen-1-yl)-1,3-thiazol-3-ium di(toluenesulfonate)

3-ethyl-2-(2-{4-[ethyl(2-{2-[ethyl({4-[2-(3-ethyl-1,3-thiazol-3-ium-2-yl)diazen-1-yl]phenyl})amino]-ethoxy}ethyl)amino]phenyl}diazen-1-yl)-1,3-thiazol-3-ium di(methyl sulfate)

3-ethyl-2-(2-{4-[ethyl(2-{2-[ethyl({4-[2-(3-ethyl-1,3-thiazol-3-ium-2-yl)diazen-1-yl]phenyl})amino]-ethoxy}ethyl)amino]phenyl}diazen-1-yl)-1,3-thiazol-3-ium tetrachlorozincate 3-methyl-2-{2-[4-(10-{4-[2-(3-methyl-1,3-thiazol-3-ium-2-yl)diazen-1-yl]phenyl}-4,7-dioxa-1,10-diazadecan-1-yl)phenyl]diazen-1-yl}-1,3-thiazol-3-ium dichloride 3-methyl-2-{2-[4-(10-{4-[2-(3-methyl-1,3-thiazol-3-ium-2-yl)diazen-1-yl]phenyl}-4,7-dioxa-1,10-diazadecan-1-yl)phenyl]diazen-1-yl}-1,3-thiazol-3-ium dibromide 3-methyl-2-{2-[4-(10-{4-[2-(3-methyl-1,3-thiazol-3-ium-2-yl)diazen-1-yl]phenyl}-4,7-dioxa-1,10-diazadecan-1-yl)phenyl]diazen-1-yl}-1,3-thiazol-3-ium sulfate 3-methyl-2-{2-[4-(10-{4-[2-(3-methyl-1,3-thiazol-3-ium-2-yl)diazen-1-yl]phenyl}-4,7-dioxa-1,10-diazadecan-1-yl)phenyl]diazen-1-yl}-1,3-thiazol-3-ium di(toluenesulfonate)

3-methyl-2-{2-[4-(10-{4-[2-(3-methyl-1,3-thiazol-3-ium-2-yl)diazen-1-yl]phenyl}-4,7-dioxa-1,10-diazadecan-1-yl)phenyl]diazen-1-yl}-1,3-thiazol-3-ium di(methyl sulfate)

3-methyl-2-{2-[4-(10-{4-[2-(3-methyl-1,3-thiazol-3-ium-2-yl)diazen-1-yl]phenyl}-4,7-dioxa-1,10-diazadecan-1-yl)phenyl]diazen-1-yl}-1,3-thiazol-3-ium tetrachlorozincate 3-methyl-2-{2-[4-(11-{4-[2-(3-methyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium dichloride 3-methyl-2-{2-[4-(11-{4-[2-(3-methyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium dibromide 3-methyl-2-{2-[4-(11-{4-[2-(3-methyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium sulfate 3-methyl-2-{2-[4-(11-{4-[2-(3-methyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium di(toluenesulfonate)

3-methyl-2-{2-[4-(11-{4-[2-(3-methyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium di(methyl sulfate)

3-methyl-2-{2-[4-(11-{4-[2-(3-methyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium tetrachlorozincate 3-methyl-2-{2-[4-(12-{4-[2-(3-methyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium dichloride 3-methyl-2-{2-[4-(12-{4-[2-(3-methyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium dibromide 3-methyl-2-{2-[4-(12-{4-[2-(3-methyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium sulfate 3-methyl-2-{2-[4-(12-{4-[2-(3-methyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium di(toluenesulfonate)

3-methyl-2-{2-[4-(12-{4-[2-(3-methyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium di(methyl sulfate)

3-methyl-2-{2-[4-(12-{4-[2-(3-methyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium tetrachlorozincate 3-ethyl-2-{2-[4-(10-{4-[2-(3-ethyl-1,3-thiazol-3-ium-2-yl)diazen-1-yl]phenyl}-4,7-dioxa-1,10-diazadecan-1-yl)phenyl]diazen-1-yl}-1,3-thiazol-3-ium dichloride 3-ethyl-2-{2-[4-(10-{4-[2-(3-ethyl-1,3-thiazol-3-ium-2-yl)diazen-1-yl]phenyl}-4,7-dioxa-1,10-diazadecan-1-yl)phenyl]diazen-1-yl}-1,3-thiazol-3-ium dibromide 3-ethyl-2-{2-[4-(10-{4-[2-(3-ethyl-1,3-thiazol-3-ium-2-yl)diazen-1-yl]phenyl}-4,7-dioxa-1,10-diazadecan-1-yl)phenyl]diazen-1-yl}-1,3-thiazol-3-ium sulfate 3-ethyl-2-{2-[4-(10-{4-[2-(3-ethyl-1,3-thiazol-3-ium-2-yl)diazen-1-yl]phenyl}-4,7-dioxa-1,10-diazadecan-1-yl)phenyl]diazen-1-yl}-1,3-thiazol-3-ium di(toluenesulfonate)

3-ethyl-2-{2-[4-(10-{4-[2-(3-ethyl-1,3-thiazol-3-ium-2-yl)diazen-1-yl]phenyl}-4,7-dioxa-1,10-diazadecan-1-yl)phenyl]diazen-1-yl}-1,3-thiazol-3-ium di(methyl sulfate)

3-ethyl-2-{2-[4-(10-{4-[2-(3-ethyl-1,3-thiazol-3-ium-2-yl)diazen-1-yl]phenyl}-4,7-dioxa-1,10-diazadecan-1-yl)phenyl]diazen-1-yl}-1,3-thiazol-3-ium tetrachlorozincate 3-ethyl-2-{2-[4-(11-{4-[2-(3-ethyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium dichloride 3-ethyl-2-{2-[4-(11-{4-[2-(3-ethyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium dibromide 3-ethyl-2-{2-[4-(11-{4-[2-(3-ethyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium sulfate 3-ethyl-2-{2-[4-(11-{4-[2-(3-ethyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium di(toluenesulfonate)

3-ethyl-2-{2-[4-(11-{4-[2-(3-ethyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium di(methyl sulfate)

3-ethyl-2-{2-[4-(11-{4-[2-(3-ethyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium tetrachlorozincate 3-ethyl-2-{2-[4-(12-{4-[2-(3-ethyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium dichloride 3-ethyl-2-{2-[4-(12-{4-[2-(3-ethyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium dibromide 3-ethyl-2-{2-[4-(12-{4-[2-(3-ethyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium sulfate 3-ethyl-2-{2-[4-(12-{4-[2-(3-ethyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium di(toluenesulfonate)

3-ethyl-2-{2-[4-(12-{4-[2-(3-ethyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium di(methyl sulfate) and/or 3-ethyl-2-{2-[4-(12-{4-[2-(3-ethyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium tetrachlorozincate.

Within the scope of the work leading to an exemplary embodiment of the present disclosure, it emerged that especially intense colors in the blue range could be achieved with the direct dyes (a) of the formula (I), when R1, R4 independently of one another stand for a methyl group or an ethyl group, R2, R3 independently of one another stand for a methyl group or for an ethyl group, R5, R6, R7, R8 each stand for a hydrogen atom, Q stands for a grouping of the formula (II), $$*-(CH_2)_n-* \qquad (II)$$

and n stands for the number 3 or 4.

Explicitly very especially preferred, therefore, are agents in accordance with an exemplary embodiment of the present disclosure for dyeing keratinic fibers, which contain at least one dye (a) of the formula (I) that is selected from the group comprising

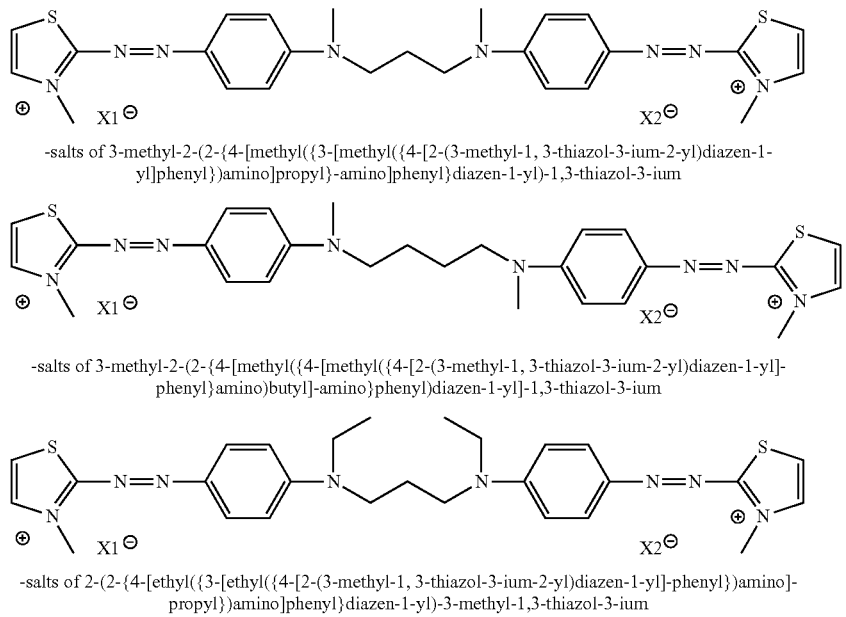

-salts of 3-methyl-2-(2-{4-[methyl({3-[methyl({4-[2-(3-methyl-1, 3-thiazol-3-ium-2-yl)diazen-1-yl]phenyl})amino]propyl}-amino]phenyl}diazen-1-yl)-1,3-thiazol-3-ium -salts of 3-methyl-2-(2-{4-[methyl({4-[methyl({4-[2-(3-methyl-1, 3-thiazol-3-ium-2-yl)diazen-1-yl]-phenyl}amino)butyl]-amino}phenyl)diazen-1-yl]-1,3-thiazol-3-ium -salts of 2-(2-{4-[ethyl({3-[ethyl({4-[2-(3-methyl-1, 3-thiazol-3-ium-2-yl)diazen-1-yl]-phenyl})amino]-propyl})amino]phenyl}diazen-1-yl)-3-methyl-1,3-thiazol-3-ium

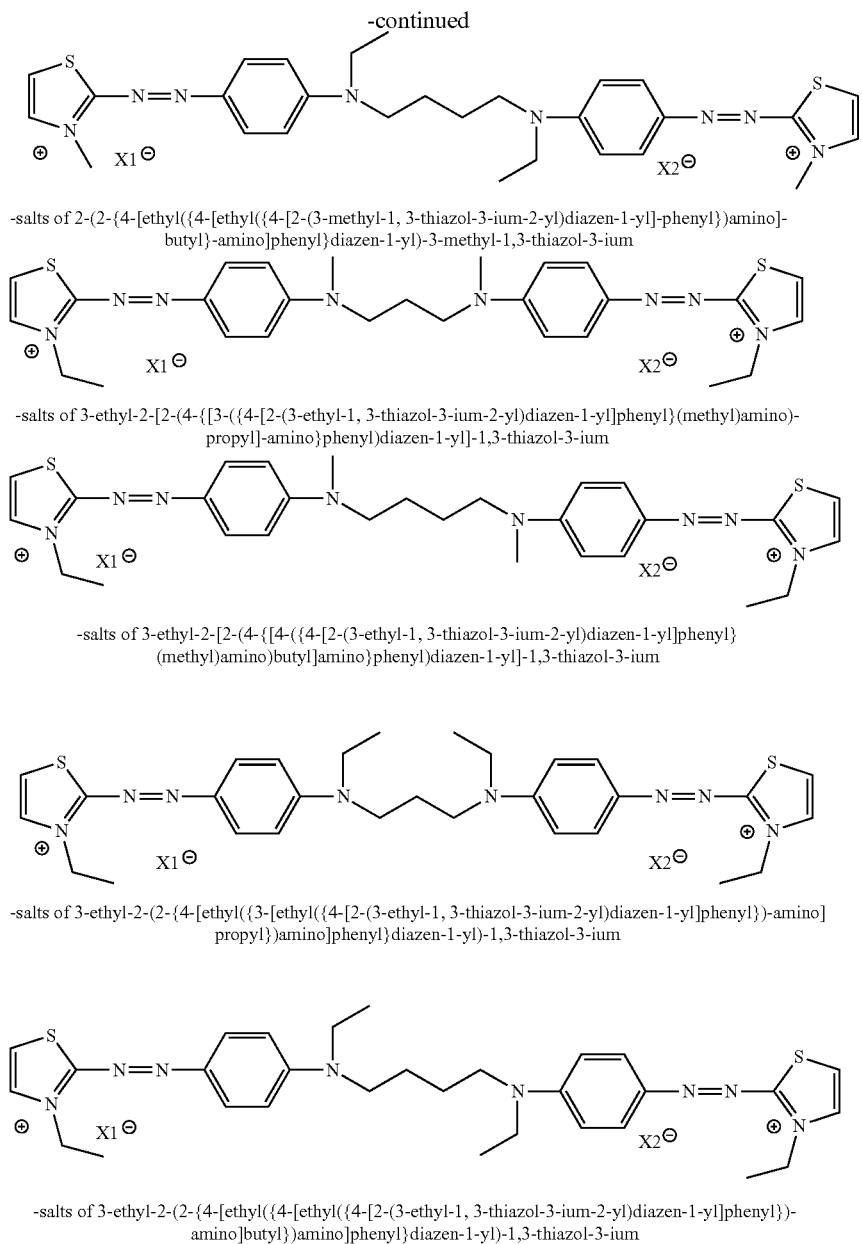

-salts of 2-(2-{4-[ethyl({4-[ethyl({4-[2-(3-methyl-1, 3-thiazol-3-ium-2-yl)diazen-1-yl]-phenyl})amino]-butyl}-amino]phenyl}diazen-1-yl)-3-methyl-1,3-thiazol-3-ium -salts of 3-ethyl-2-[2-(4-{[3-({4-[2-(3-ethyl-1, 3-thiazol-3-ium-2-yl)diazen-1-yl]phenyl}(methyl)amino)-propyl]-amino}phenyl)diazen-1-yl]-1,3-thiazol-3-ium -salts of 3-ethyl-2-[2-(4-{[4-({4-[2-(3-ethyl-1, 3-thiazol-3-ium-2-yl)diazen-1-yl]phenyl}(methyl)amino)butyl]amino}phenyl)diazen-1-yl]-1,3-thiazol-3-ium -salts of 3-ethyl-2-(2-{4-[ethyl({3-[ethyl({4-[2-(3-ethyl-1, 3-thiazol-3-ium-2-yl)diazen-1-yl]phenyl})-amino]propyl})amino]phenyl}diazen-1-yl)-1,3-thiazol-3-ium -salts of 3-ethyl-2-(2-{4-[ethyl({4-[ethyl({4-[2-(3-ethyl-1, 3-thiazol-3-ium-2-yl)diazen-1-yl]phenyl})-amino]butyl})amino]phenyl}diazen-1-yl)-1,3-thiazol-3-ium The agents in accordance with an exemplary embodiment of the present disclosure for dyeing keratinic fibers contain the direct dye(s) of the formula (I) primarily in a total amount of about 0.01 to about 4.5% by weight, preferably of about 0.05 to about 2.8% by weight, more preferably of about 0.1 to about 2.2% by weight, and particularly preferably of about 0.2 to about 1.2% by weight. The quantitative data in percent by weight here refer to the total amount of all compounds of the formula (I) which are contained in the agent and are placed in relation to the total weight of the agent.

In a further preferred embodiment, an agent of the present disclosure for dyeing keratinic fibers is therefore characterized in that, based on the total weight of the agent, it contains one or more direct dyes (a) of the formula (I) in a total amount of about 0.01 to about 4.5% by weight, preferably of about 0.05 to about 2.8% by weight, more preferably of about 0.1 to about 2.2% by weight, and particularly preferably of about 0.2 to about 1.2% by weight.

The dyes of the general formula (I) can be produced, for example, by a method as described in WO 2002/100369 A2.

Thus, for example, the educt 2-aminothiazole can be converted into the diazonium ion in concentrated sulfuric acid with nitrosylsulfuric acid:

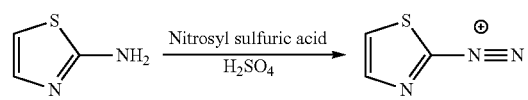 [SMILES: Nc1nccs1 ; "H2SO4" ; N#[N+]c1nccs1]

The reactive diazonium ion then enters into a double azo coupling reaction with dimeric aniline derivatives:

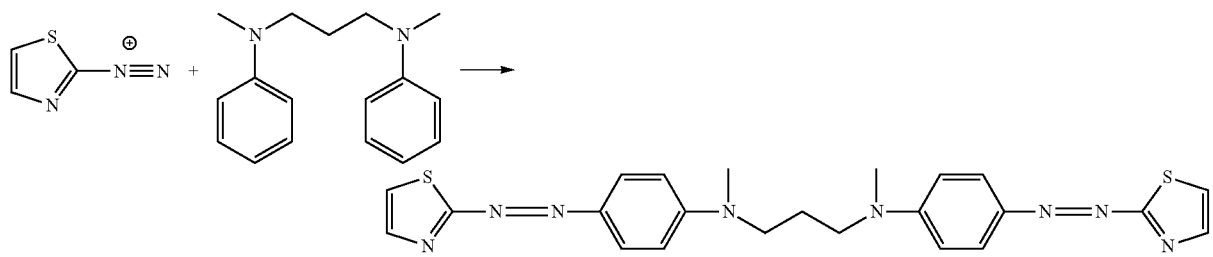

The neutral dimeric dye arising in the azo coupling reaction can then be finally doubly quaternized with quaternizing agents. The quaternization reaction is preferably carried out in a polar aprotic solvent (such as, for example, DMSO, DMF, etc.). For example, dimethyl sulfate, methyl iodide, or p-toluenesulfonate may be used as quaternizing agents.

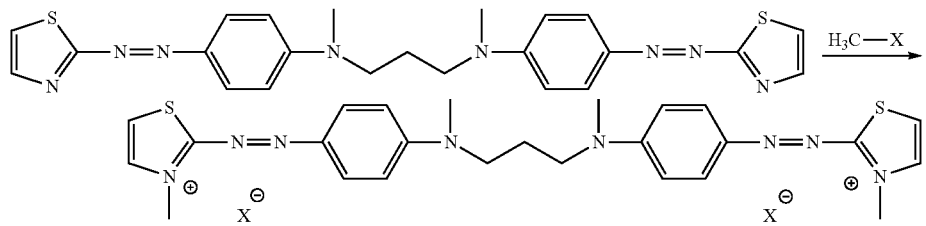

The agents for dyeing keratinic fibers contain at least one nonionic surfactant as the second component (b) essential to an exemplary embodiment of the present disclosure.

Surfactants are amphiphilic (bifunctional) compounds, which consist of at least one hydrophobic and at least one hydrophilic moiety. The hydrophobic group is preferably a hydrocarbon chain having 12-30 carbon atoms, which may be saturated or unsaturated, linear or branched. This C12-C30 alkyl chain is particularly preferably linear. In the case of nonionic surfactants, the hydrophilic moiety comprises an uncharged hydrophilic head group, which has strong dipole moments and is highly hydrated in aqueous solution.

Nonionic surfactants contain as the hydrophilic group, e.g., a polyol group, a polyalkylene glycol ether, or a combination of polyol and polyglycol ether group. Such compounds are, for example, adducts of 2 to 100 mol of ethylene oxide and/or 2 to 100 mol of propylene oxide to linear and branched fatty alcohols having 12 to 30 C atoms, fatty alcohol polyglycol ethers or fatty alcohol polypropylene glycol ethers or mixed fatty alcohol polyethers, adducts of 2 to 100 mol of ethylene oxide and/or 2 to 100 mol of propylene oxide to linear and branched fatty acids having 12 to 30 C atoms, fatty acid polyglycol ethers or fatty acid polypropylene glycol ethers or mixed fatty acid polyethers, adducts of 2 to 50 mol of ethylene oxide and/or 2 to 50 mol of propylene oxide to linear and branched alkylphenols having 8 to 15 C atoms in the alkyl group, alkyl phenol polyglycol ethers or alkyl phenol polypropylene glycol ethers or mixed alkyl phenol polyethers, an adduct, end-capped with a methyl or C2-C6 alkyl group, of 2 to 50 mol of ethylene oxide and/or 1 to 5 mol of propylene oxide to linear and branched fatty alcohols having 12 to 30 C atoms, to fatty acids having 8 to 30 C atoms, and to alkyl phenols having 8 to 15 C atoms in the alkyl group, C12-C30 fatty acid monoesters and diesters of adducts of 1 to 30 mol of ethylene oxide to glycerol, adducts of 5 to 60 mol of ethylene oxide to castor oil and hydrogenated castor oil, alkoxylated triglycerides, alkoxylated fatty acid alkyl esters of the formula (Tnio-1)

$$R^1CO—(OCH_2CHR^2)_wOR^3 \quad \text{(Tnio-1)}$$

in which

R1-CO stands for a linear or branched, saturated and/or unsaturated acyl group having 12 to 30 C atoms, R2 for hydrogen or methyl, R3 for a linear or branched $C_1$-$C_4$ alkyl group, and w for the numbers 1 to 20, amine oxides, sorbitan fatty acid esters and adducts of ethylene oxide to sorbitan fatty acid esters such as, for example, polysorbates, sugar fatty acid esters and adducts of ethylene oxide to sugar fatty acid esters, adducts of ethylene oxide to fatty acid alkanolamides, and sugar surfactants of the formula (Tnio-2)

$$R^4O\text{-}[G]_p \quad \text{(Tnio-2)}$$

in which

R2 stands for a linear $C_{12}$-$C_{30}$ alkyl group,

G stands for a sugar group having 5 or 6 carbon atoms, preferably for glucose, and p stands for an integer from 1 to 10, preferably for an integer from 1 to 6.

Fatty alcohols are explicitly not nonionic surfactants in the context of the present disclosure. Fatty alcohols in the context of the present disclosure fall within the group of fatty substances.

The treatment of keratinic fibers with agents that contained (a) at least one direct dye of the formula (I) and (b) at least one nonionic surfactant led to intense colors in attractive, pure blue shades without a red content. It emerged surprisingly in this regard that the substantivity could be optimized still further by the use of one or more special nonionic surfactants. Especially intense blue colors were obtained, if the dyes (a) of the formula (I) with at least one nonionic surfactant (b) were selected from the group comprising adducts of 2 to 100 mol of ethylene oxide and/or 2 to 100 mol of propylene oxide to linear and branched fatty alcohols having 12 to 30 C atoms, fatty alcohol polyglycol ethers or fatty alcohol polypropylene glycol ethers or mixed fatty alcohol polyethers, adducts of 2 to 100 mol of ethylene oxide and/or 2 to 100 mol of propylene oxide to linear and branched fatty acids having 12 to 30 C atoms, fatty acid polyglycol ethers or fatty acid polypropylene glycol ethers or mixed fatty acid polyethers, and the addition products of 5 to 60 mol of ethylene oxide to castor oil and hydrogenated castor oil.

In a particularly preferred embodiment, an agent of the present disclosure is therefore characterized in that it contains (b) at least one nonionic surfactant that is selected from adducts of 2 to 100 mol of ethylene oxide and/or 2 to 100 mol of propylene oxide to linear and branched fatty alcohols having 12 to 30 C atoms, fatty alcohol polyglycol ethers or fatty alcohol polypropylene glycol ethers or mixed fatty alcohol polyethers, adducts of 2 to 100 mol of ethylene oxide and/or 2 to 100 mol of propylene oxide to linear and branched fatty acids having 12 to 30 C atoms, fatty acid polyglycol ethers or fatty acid polypropylene glycol ethers or mixed fatty acid polyethers, and adducts of 5 to 60 mol of ethylene oxide to castor oil and hydrogenated castor oil.

Particularly preferred adducts of 5 to 60 mol of ethylene oxide to castor oil and hydrogenated castor oil are known, for example, under the INCI names PEG-30 Castor Oil with the CAS number 61791-12-6

PEG-40 Hydrogenated Castor Oil with the CAS number 61788-85-0.

In the case of adducts of 2 to 100 mol of ethylene oxide to linear and branched fatty alcohols having 12 to 30 C atoms, it is understood, for example, that each mole of fatty alcohol was reacted with 2 to 100 mol of ethylene oxide.

Accordingly, the adducts of 2 to 100 mol of ethylene oxide to C12-C30 fatty alcohols are compounds of the general formula (B1)

(B1)

where

R10 stands for a linear or branched $C_{12}$-$C_{30}$ alkyl group and x stands for an integer from 2 to 100.

The adducts of 2 to 100 mol of ethylene oxide to linear and branched fatty acids having 12 to 30 C atoms are compounds of the general formula (B2)

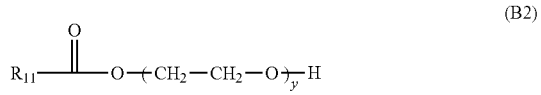

(B2)

where

R11 stands for a linear or branched C-$C_{29}$ alkyl group y stands for an integer from 2 to 100.

Within the group of the tested nonionic surfactants, the greatest increase in color intensity could be observed with the compounds of the general formula (B1) and/or (B2), if these nonionic surfactants were dyed in combination with at least one dye of the general formula (I).

In a particularly preferred embodiment, an agent of the present disclosure is therefore characterized in that it contains as nonionic surfactant (b) at least one compound of the formula (B1) and/or at least one compound of the formula (B2),

(B1)

where

R10 stands for a linear or branched $C_{12}$-$C_{30}$ alkyl group and x stands for an integer from 2 to 100,

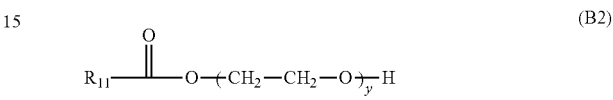

(B2)

where

R11 stands for a linear or branched $C_{11}$-$C_{29}$ alkyl group and y stands for an integer from 2 to 100.

The very best absorption capacity could be observed, if a compound of the formula (B1) in which x stands for an integer from 10 to 50 was used as nonionic surfactant (b).

In an explicitly very particularly preferred embodiment, an agent of the present disclosure is, therefore, characterized in that it contains as nonionic surfactant (b) at least one compound of the formula (B1),

(B1)

where

R10 stands for a linear or branched $C_{12}$-$C_{30}$ alkyl group and x stands for an integer from 10 to 50.

Particularly preferred surfactants of this embodiment are known, for example, under the INCI names Ceteareth-12 (C16/C18 fatty alcohols, ethoxylated with 12 EO)

Ceteareth-20 (C16/C18 fatty alcohols, ethoxylated with 20 EO)

Ceteareth-30 (C16/C18 fatty alcohols, ethoxylated with 30 EO).

by weight, more preferably of 2.0 to 4.5% by weight, and very particularly preferably of 2.5 to 4.5% by weight.

Furthermore, the agents in accordance with an exemplary embodiment of the present disclosure can also contain one or more cationic surfactants. Cationic surfactants are understood to be surfactants, therefore, surface-active compounds, in each case with one or more positive charges. Cationic surfactants contain only positive charges. Typically, these surfactants are made up of a hydrophobic part and a hydrophilic head group, wherein the hydrophobic part normally consists of a hydrocarbon skeleton (e.g., consisting of one or two linear or branched alkyl chains), and the positive charge(s) is (are) localized in the hydrophilic head group. Cationic surfactants adsorb at interfaces and aggregate in aqueous solution above the critical micelle formation concentration to form positively charged micelles.

Examples of cationic surfactants are quaternary ammonium compounds, which can carry as hydrophobic groups one or two alkyl chain with a chain length of 8 to 28 C atoms, quaternary phosphonium salts, substituted with one or more alkyl chains with a chain length of 8 to 28 C atoms, or tertiary sulfonium salts.

Furthermore, the cationic charge in the form of an onium structure as well can be part of a heterocyclic ring (e.g., an imidazolium ring or a pyridinium ring).

Apart from the functional unit carrying the cationic charge, the cationic surfactant can also contain other uncharged functional groups; this is the case in esterquats, for example.

Suitable cationic surfactants of this type are, for example, physiologically acceptable salts of N,N,N-trimethyl-1-hexadecanaminium, in particular N,N,N-trimethyl-1-hexadecanaminium chloride, which is also marketed under the trade name Dehyquart A-CA.

Another suitable cationic surfactant is a physiologically acceptable salt of dimethyl distearyl dimethyl ammonium, particularly preferably dimethyl distearyl ammonium chloride.

Other cationic surfactants can be selected from the group of the cationic imidazolium compounds.

The agents in accordance with an exemplary embodiment of the present disclosure can contain the cationic surfactant (s) in a total amount of about 0.1 to about 4.8% by weight, preferably of about 0.2 to about 2.4% by weight, more preferably of about 0.3 to about 1.8% by weight, based on the total weight of the agent.

Agents suitable according to an exemplary embodiment of the present disclosure can be characterized, furthermore, in that that they contain in addition at least one zwitterionic surfactant. Suitable zwitterionic surfactants are betaines, N-alkyl-N,N-dimethylammonium glycinates, N-acylaminopropyl-N,N-dimethylammonium glycinates, and 2-alkyl-3-carboxymethyl-3-hydroxyethyl imidazolines. A preferred zwitterionic surfactant is known by the INCI name Cocamidopropyl Betaine.

Agents suitable according to an exemplary embodiment of the present disclosure are characterized in that the agent contains in addition at least one amphoteric surfactant. Preferred amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids. Particularly preferred amphoteric surfactants are N-cocoalkyl aminopropionate, cocoacylaminoethyl aminopropionate, and C12-C18 acylsarcosine.

In another preferred embodiment, the agents of the present disclosure contain apart from the compound of the formula (I) in addition at least one other direct dye. The achievable shade spectrum can be broadened by the combination with other cationic direct dyes, and the color properties can be improved still further.

Direct dyes can be divided into anionic, cationic, and nonionic direct dyes.

The direct dyes are preferably selected from the cationic direct dyes, because these are highly compatible with dyes of the general formula (I).

In another particularly preferred embodiment, an agent of the present disclosure is characterized in that it contains in addition at least one other cationic direct dye that is different from the dyes of the formula (I).

Cationic dyes in this regard are understood to be dyes that carry at least one positive charge.

One or more dyes from the group comprising Basic Yellow 87, Basic Orange 31, Basic Red 51, Basic Violet 2, and Cationic Blue 347 have proven to be especially highly compatible.

Very particularly highly compatible are the dyes of the formula (I) with the cationic azo dyes, Basic Orange 31 and Basic Red 51. Shades, other than purely yellow shades, over the entire color spectrum can be produced by combination of a dye of the formula (I) with Basic Orange 31 and/or Basic Red 51.

In another particularly preferred embodiment, an agent of the present disclosure is characterized in that it contains in addition Basic Orange 31 and/or Basic Red 51.

The agent in accordance with an exemplary embodiment of the present disclosure, however, can also contain in addition at least one nonionic direct dye. These can be selected from the group comprising HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-bis(2-hydroxyethyl)amino-2-nitrobenzene, 3-nitro-4-(2-hydroxy-ethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, und 2-chloro-6-ethylamino-4-nitrophenol.

In addition, anionic direct dyes may also be present, which are known under the international names or trade names: Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue, and tetrabromophenol blue. The agents in accordance with an exemplary embodiment of the present disclosure can also be used, furthermore, together with oxidation dyeing agents. Oxidation dyeing agents of this type contain in addition at least one oxidation dye precursor, preferably at least one oxidation dye precursor of the developer type and at least one oxidation dye precursor of the coupler type. Especially suitable oxidation dye precursors of the developer type are selected in this case from at least one compound from the group formed by p-phenylenediamine, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis(2-hydroxyethyl)-N,N'-bis(4-aminophenyl)-1,3-diaminopropan-2-ol, bis(2-hydroxy-5-aminophenyl)methane, 1,3-bis(2,5-diaminophenoxy)propan-2-ol, N,N'-bis(4-aminophenyl)-1,4-diazacycloheptane, 1,10-bis(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, and the physiologically acceptable salts thereof.

Especially suitable oxidation dye precursors of the coupler type in this case are selected from the group, formed by 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)

amino-2-methylphenol, 2,4-dichloro-3-aminophenol, 2-aminophenol, 3-phenylenediamine, 2-(2,4-diamino-phenoxy)ethanol, 1,3-bis(2,4-diaminophenoxy)propane, 1-methoxy-2-amino-4-(2-hydroxyethylamino)-benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxy-ethoxy)-5-methylphenylamine, 1-amino-3-bis(2-hydroxyethyl)aminobenzene, resorcinol, 2-methyl-resorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxy-pyridine, 1-phenyl-3-methylpyrazol-2-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of these compounds, or the physiologically acceptable salts thereof.

The additional direct dyes, developer components, and coupler components are preferably each used in a proportion of about 0.0001 to about 5.0% by weight, preferably about 0.001 to about 3.5% by weight, based in each case on the ready-to-use agent. In this case, developer components and coupler components are generally used in approximately molar amounts to one another. Although molar use has proven to be expedient, a certain excess of individual oxidation dye precursors is not disadvantageous, so that developer components and coupler components may have a molar ratio of about 1 to 0.5 to about 1 to 3, particularly about 1 to 1 to about 1 to 2.

If the dyeing with the direct dyes of the formula (I) in accordance with an exemplary embodiment of the present disclosure and an oxidative lightening of the keratin fibers is to occur in one step, thus the agents contain in addition an oxidizing agent, preferably hydrogen peroxide and/or one of its solid adducts to organic or inorganic compounds.

In a preferred embodiment, hydrogen peroxide itself is used as an aqueous solution. The concentration of a hydrogen peroxide solution in the agent according to an exemplary embodiment of the present disclosure is determined, on the one hand, by legal requirements and, on the other, by the desired effect; preferably, about 6 to about 12% by weight solutions in water are used. Ready-to-use agents of the first subject of the present disclosure, which are preferred according to an exemplary embodiment of the present disclosure, are characterized in that, based on the total weight of the ready-to-use agent, they contain about 0.5 to about 20% by weight, preferably about 1 to about 12.5% by weight, particularly preferably about 2.5 to about 10% by weight, and in particular about 3 to about 6% by weight of hydrogen peroxide, based in each case on the total weight of the agent.

In a further particularly preferred embodiment, an agent of the present disclosure is characterized in that it contains, based on the total weight of the agent, about 0.5 to about 12.5% by weight, preferably about 2.5 to about 10% by weight, and in particular about 3 to about 6% by weight of hydrogen peroxide.

To achieve an intensified lightening and bleaching effect, the agent can contain furthermore at least one peroxo salt. Suitable peroxo salts are inorganic peroxo compounds, preferably selected from the group formed by ammonium peroxodisulfate, alkali metal peroxodisulfates, ammonium peroxomonosulfate, alkali metal peroxomonosulfates, alkali metal peroxodiphosphates, and alkaline earth metal peroxides. Peroxodisulfates, in particular ammonium peroxodisulfate, potassium peroxodisulfate, and sodium peroxodisulfate are particularly preferred.

In another particularly preferred embodiment, an agent of the present disclosure is characterized in that it contains in addition at least one persulfate from the group comprising ammonium peroxodisulfate, potassium peroxodisulfate, and sodium peroxodisulfate.

The agent in accordance with an exemplary embodiment of the present disclosure contains the persulfates in each case in an amount from about 0.5 to about 20% by weight, preferably about 1 to about 12.5% by weight, particularly preferably about 2.5 to about 10% by weight, and in particular about 3 to about 6% by weight, based on the total weight of the ready-to-use agent.

In order to intensify the blonding effect, the dyeing and/or delustering agent can contain further bleach boosters such as, for example, tetraacetylethylenediamine (TAED), 1,5-diacetyl-2,4-dioxohexahydro-1,3,5-triazine (DADHT), tetraacetyl glycoluril (TAGU), N-nonanoylsuccinimide (NOSI), n-nonanoyl- or isononanoyloxybenzenesulfonate (n- or i-NOBS), phthalic anhydride, triacetin, ethylene glycol diacetate, and 2,5-diacetoxy-2,5-dihydrofuran, and carbonate salts or hydrogen carbonate salts, in particular ammonium hydrogen carbonate, ammonium carbonate, sodium hydrogen carbonate, disodium carbonate, potassium hydrogen carbonate, dipotassium carbonate, and calcium carbonate, and nitrogen-containing, heterocyclic bleach boosters, such as 4-acetyl-1-methylpyridinium-p-toluenesulfonate, 2-acetyl-1-methylpyridinium-p-toluenesulfonate, and N-methyl-3,4-dihydroisoquinolinium-p-toluenesulfonate.

To further enhance the lightening, at least one $SiO_2$ compound, such as silicic acid or silicates, in particular water glasses, can be added in addition to the composition in accordance with an exemplary embodiment of the present disclosure. It can be preferred according to an exemplary embodiment to use the $SiO_2$ compounds in amounts of about 0.05% by weight to about 15% by weight, particularly preferably in amounts of about 0.15% by weight to about 10% by weight, and very particularly preferably in amounts of about 0.2% by weight to about 5% by weight, based in each case on the anhydrous composition in accordance with an exemplary embodiment of the present disclosure. The quantitative data in this case indicate the content of the $SiO_2$ compounds (without their water component) in the agents.

The dyeing agents, furthermore, can contain additional active substances, auxiliary substances, and additives in order to improve the coloring performance and to set other desired properties of the agents.

The dyeing agents are preferably provided as a liquid preparation and another surface-active substance is therefore optionally added in addition to the agents, wherein such surface-active substances are called surfactants or emulsifiers depending on the field of application: They are preferably selected from anionic, zwitterionic, amphoteric, and nonionic surfactants and emulsifiers.

The dyeing agents in accordance with an exemplary embodiment of the present disclosure can contain other auxiliary substances and additives. Thus, it has proven advantageous for the agents to contain at least one thickener. There are no basic restrictions in regard to these thickeners. Both organic and purely inorganic thickeners may be used.

Suitable thickeners are
anionic, synthetic polymers;
cationic, synthetic polymers;
naturally occurring thickeners, such as nonionic guar gums, scleroglucan gums orxanthan gums, gum arabic, gum ghatti, karaya gum, tragacanth gum, carrageenan gum, agar-agar, locust bean flour, pectins, alginates, starch fractions, and derivatives such as amylose, amylopectin, and dextrins, as well as cellulose derivatives such as, for example, methylcellulose, carboxyalkylcelluloses, and hydroxyalkylcelluloses;
nonionic, fully synthetic polymers such polyvinyl alcohol or polyvinylpyrrolidinone; as well as
inorganic thickeners, in particular phyllosilicates such as, for example, bentonite, in particular smectites, such as montmorillonite or hectorite.

Dyeing processes on keratin fibers typically take place in an alkaline environment. To treat keratin fibers and the skin as well as gently as possible, setting a too high pH value is not desirable, however. It is preferred, therefore, if the pH value of the ready-to-use agent is between about 7 and about 11, in particular between about 8 and about 10.5. pH values in the context of an exemplary embodiment of the present disclosure are pH values measured at a temperature of about 22° C.

The alkalinizing agents that can be used for adjusting the preferred pH value according to an exemplary embodiment of the present disclosure can be selected from the group formed by ammonia, alkanolamines, basic amino acids, and inorganic alkalinizing agents such as alkali (alkaline earth) metal hydroxides, alkali (alkaline earth) metal metasilicates, alkali (alkaline earth) metal phosphates, and alkali (alkaline earth) metal hydrogen phosphates. Preferred inorganic alkalinizing agents are magnesium carbonate, sodium hydroxide, potassium hydroxide, sodium silicate, and sodium metasilicate. Organic alkalinizing agents that can be used according to an exemplary embodiment off the present disclosure are preferably selected from monoethanolamine, 2-amino-2-methylpropanol, and triethanolamine. The basic amino acids that can be used as alkalinizing agents in accordance with an exemplary embodiment of the present disclosure are preferably selected from the group formed by arginine, lysine, ornithine, and histidine, especially preferably arginine. It emerged in the context of studies, however, that, furthermore, agents preferred according to an exemplary embodiment of the present disclosure are characterized in that they contain in addition an organic alkalinizing agent. An embodiment of the first subject of the present disclosure is characterized in that the agent contains in addition at least one alkalinizing agent, which is selected from the group formed by ammonia, alkanolamines, and basic amino acids, particularly by ammonia, monoethanolamine, and arginine, or the acceptable salts thereof.

It has proven to be advantageous, furthermore, if the dyeing agents, particularly if they contain hydrogen peroxide in addition, contain at least one stabilizer or complexing agent. Especially preferred stabilizers are phenacetin, alkali benzoates (sodium benzoate), and salicylic acid. Furthermore, all complexing agents in the prior art can be used. Complexing agents preferred according to an exemplary embodiment of the present disclosure are nitrogen-containing polycarboxylic acids, particularly EDTA and EDDS, and phosphonates, particularly 1-hydroxyethane-1,1-diphosphonate (HEDP), and/or ethylenediamine tetramethylene phosphonate (EDTMP), and/or diethylenetriamine pentamethylene phosphonate (DTPMP), or sodium salts thereof.

Further, the agents in accordance with an exemplary embodiment of the present disclosure can contain other active substances, auxiliary substances, and additives such as, for example, nonionic polymers such as, for example, vinylpyrrolidinone/vinyl acrylate copolymers, polyvinylpyrrolidinone, vinylpyrrolidinone/vinyl acetate copolymers, polyethylene glycols, and polysiloxanes; additional silicones such as volatile or nonvolatile, straight-chain, branched or cyclic, crosslinked or noncrosslinked polyalkylsiloxanes (such as dimethicones or cyclomethicones), polyarylsiloxanes, and/or polyalkylarylsiloxanes, particularly polysiloxanes with organofunctional groups, such as substituted or unsubstituted amines (amodimethicones), carboxyl, alkoxy, and/or hydroxyl groups (dimethicone copolyols), linear polysiloxanes (A)-polyoxyalkylene (B) block copolymers, grafted silicone polymers; cationic polymers such as quaternized cellulose ethers, polysiloxanes with quaternary groups, dimethyldiallylammonium chloride polymers, acrylamide-dimethyldiallylammonium chloride copolymers, dimethylaminoethyl methacrylate-vinylpyrrolidinone copolymers quaternized with diethylsulfate, vinylpyrrolidinone-imidazolinium-methochloride copolymers, and quaternized polyvinyl alcohol; zwitterionic and amphoteric polymers; anionic polymers such as, for example, polyacrylic acids or crosslinked polyacrylic acids; structurants such as glucose, maleic acid, and lactic acid, hair-conditioning compounds such as phospholipids, for example, lecithin and kephalins; perfume oils, dimethyl isosorbide, and cyclodextrins; fiber-structure-improving active substances, particularly mono-, di-, and oligosaccharides such as, for example, glucose, galactose, fructose, fruit sugar, and lactose; dyes for coloring the agent; antidandruff agents such as piroctone olamine, zinc omadine, and climbazole; amino acids and oligopeptides; protein hydrolysates with an animal and/or vegetable base, and in the form of their fatty acid condensation products or optionally anionically or cationically modified derivatives; vegetable oils; light stabilizers and UV blockers; active substances such as panthenol, pantothenic acid, pantolactone, allantoin, pyrrolidinone carboxylic acids, and salts thereof, as well as bisabolol; polyphenols, particularly hydroxycinnamic acids, 6,7-dihydroxycoumarins, hydroxybenzoic acids, catechins, tannins, leukoanthocyanidins, anthocyanidins, flavanones, flavones, and flavonols; ceramides or pseudoceramides; vitamins, provitamins, and vitamin precursors; plant extracts; fats and waxes such as fatty alcohols, beeswax, montan wax, and paraffins; swelling and penetration agents such as glycerol, propylene glycol monoethyl ethers, carbonates, hydrogen carbonates, guanidines, ureas, and primary, secondary, and tertiary phosphates; opacifiers such as latex, styrene/PVP and styrene/acrylamide copolymers; pearlescent agents such as ethylene glycol mono- and distearate and PEG-3 distearate; pigments and propellants such as propane-butane mixtures, N2O, dimethyl ether, CO2, and air.

The selection of these additional substances is made by the skilled artisan according to the desired properties of the agents. In regard to other facultative components and the employed amounts of said components, reference is made expressly to relevant handbooks known to the skilled artisan. The additional active and auxiliary substances are used in the agents in accordance with an exemplary embodiment of the present disclosure preferably in amounts in each case of about 0.0001 to about 25% by weight, in particular of about 0.0005 to about 15% by weight, based on the total weight of the application mixture.

Keratinic fibers can be dyed in exceptionally attractive and intense blue tints with the dyeing agents, containing direct dyes in accordance with an exemplary embodiment of the present disclosure of the general formula (I). The dyes of the general formula (I) are cationic dimeric azo dyes. In this case, it emerged surprisingly that the color intensity of cationic azo dyes can be increased still further by the addition of one or more nonionic surfactants (b) of the formula (B1),

$$R_{10}\text{—}O\text{—}(CH_2\text{—}CH_2\text{—}O)_x\text{—}H \quad (B1)$$

where

R10 stands for a linear or branched $C_{12}$-$C_{30}$ alkyl group and x stands for an integer from 2 to 100.

A second subject of the present disclosure, therefore, is the use of one or more nonionic surfactants (b) of the formula (B1)

$$R_{10}\text{—}O\text{—}(CH_2\text{—}CH_2\text{—}O)_x\text{—}H \quad (B1)$$

where

R10 stands for a linear or branched $C_{12}$-$C_{30}$ alkyl group and x stands for an integer from 2 to 100, for improving the substantivity of cationic azo dyes on keratinic fibers.

Improvement of substantivity in this regard is understood to mean that the dyes diffuse increasingly or more greatly into the keratinic fibers, which leads to colors with a higher color intensity. The greater color intensity can be detected either visually by examination under a daylight lamp or, however, by colorimetric measurement (determination of the Lab values).

Suitable cationic azo dyes are, for example, the dyes Basic Yellow, Basic Orange 31, and Basic Red 51.

The intensification of the color absorption by the nonionic surfactants of the formula (B1) works in fact in principle in the case of all cationic azo dyes. The color absorption of the dyes of the general formula (I), however, can be improved especially well by the addition of the nonionic surfactants of the formula (B1).

A further subject of the present disclosure, therefore, is the use of one or more nonionic surfactants (b) of the formula (B1)

$$R_{10}\text{—}O\text{—}(CH_2\text{—}CH_2\text{—}O)_x\text{—}H \quad (B1)$$

where

R10 stands for a linear or branched $C_{12}$-$C_{30}$ alkyl group and x stands for an integer from 2 to 100, for improving the substantivity of direct dyes of the formula (I), as they are disclosed in detail in the description of the first subject of the present disclosure, on keratinic fibers.

The agents in accordance with an exemplary embodiment of the present disclosure can be formulated and used accordingly as one-component agents or as multicomponent agents such as two-component agents or three-component agents. Separation into multicomponent systems is appropriate in particular when incompatibilities of the ingredients are a possibility or a risk; in the case of such systems, the agent to be used is prepared by the consumer immediately before use by mixing the components.

The agent in accordance with an exemplary embodiment of the present disclosure for changing the color of keratinic fibers is always understood to be the ready-to-use agent.

If the agent in accordance with an exemplary embodiment is provided to the user in the form of a one-component agent, then the ready-to-use agent need not be prepared first, but can be removed directly from the container in which it was packaged and applied to the keratinic fibers.

Blonding agents, however, are typically two-component products, in which an oxidizing agent-containing component (A1) is mixed shortly prior to use with an (alkalizing) agent (A2) and this ready-to-use mixture is applied to hair.

In this case, the agent in accordance with an exemplary embodiment is the ready-to-use agent that was prepared shortly prior to use by mixing (A1) and (A2).

In this case, the direct dyes (a) of the general formula (I) can be packaged in component (A1) (i.e., together with the oxidizing agent) or, however, in component (A2) (together with the alkalizing agent). The nonionic surfactant(s) (b) can also be packaged in component (A1) (i.e., together with the oxidizing agent) or, however, in component (A2) (together with the alkalizing agent).

It is likewise possible and according to an exemplary embodiment of the present disclosure, if the ready-to-use agent is prepared shortly prior to application to human hair by mixing 3 components, wherein component (A1) contains at least one direct dye of the general formula (I) and at least one alkalizing agent, component (A2) contains at least one first oxidizing agent (e.g., hydrogen peroxide), and component (A3) contains at least one second oxidizing agent (e.g., one or more peroxodisulfate salts), At least one of components (A1), (A2) and (A3) in this case again contains at least one nonionic surfactant (b).

During the contact time of the agents on the fibers, it may be advantageous to assist the lightening process or delustering process by supplying heat. Heat may be supplied by an external heat source such as, e.g., warm air from a warm air blower, and also, in particular in the case of hair lightening on living subjects, by the body temperature of the subject. In the case of the latter option, the portion to be treated is usually covered with a hood. A contact phase at room temperature is likewise in accordance with an exemplary embodiment of the present disclosure. The temperature during the contact time is in particular between about 20° C. and about 40° C., in particular between about 25° C. and about 38° C. Once the contact time has ended, the remaining dye preparation is rinsed out of the hair with water or a cleansing agent. A commercial shampoo, in particular, may serve here as a cleansing agent, wherein the cleansing agent can be omitted and the rinsing-out operation can occur with water, particularly if the lightening agent possesses a highly surfactant-containing carrier.

The statements made about the agents of the present disclosure apply mutatis mutandis in regard to other preferred embodiments of the uses of the present disclosure.

EXAMPLES

Direct dye 1: 3-methyl-2-(2-{4-[methyl({3-[methyl({4-[2-(3-methyl-1,3-thiazol-3-ium-2-yl)diazen-1-yl]phenyl})amino]propyl})amino]phenyl}diazen-1-yl)-1,3-thiazol-3-ium, di(methyl sulfate) (DD 1, According to an Exemplary Embodiment of the Present Disclosure)

The dye DD 1 was synthesized using a method as described in the documents WO 2002/100369 A2 and U.S. Pat. No. 3,291,788.

2-Aminothiazole and N,N'-dimethyl-N,N'-diphenylpropane-1,3-diamine were used as educts (azo coupling reaction in aqueous, sulfuric solution with nitrosylsulfuric acid). The neutral dye formed in this azo coupling reaction was quaternized after this (for example, with the quaternizing agent dimethyl sulfate in a polar, aprotic solvent such as dimethylformamide or dimethyl sulfoxide).

DD 1 (According to an Exemplary Embodiment of the Present Disclosure)

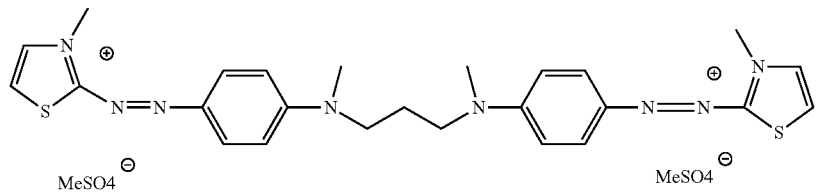

Comparative Example

Direct Dye 2: 3-methyl-2-(2-{4-[methyl({2-[methyl({4-[2-(3-methyl-1,3-thiazol-3-ium-2-yl)diazen-1-yl]phenyl})amino]ethyl})amino]phenyl}diazen-1-yl)-1,3-thiazol-3-ium di(methyl sulfate) (DD 2, Comparison)

The dye DD 2 was synthesized using a method as described in the documents WO 2002/100369 A2 and U.S. Pat. No. 3,291,788.

2-Aminothiazole and N,N'-dimethyl-N,N'-diphenylethane-1,2-diamine were used as educts (azo coupling reaction in aqueous, sulfuric solution with nitrosylsulfuric acid). The dye formed in this azo coupling reaction was quaternized after this (for example, with a quaternizing agent such as dimethyl sulfate in a polar, aprotic solvent such as dimethylformamide or dimethyl sulfoxide).

DD 2 (Comparison)

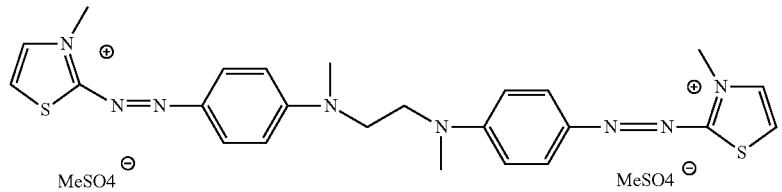

Dye Examples
Formulations

The following color creams were prepared (all quantities are given in % by weight, active substance)

|  | V1 | V2 | V3 | E1 |
|---|---|---|---|---|
| Cetearyl alcohol (C16/C18 fatty alcohol) | 1.0 | 1.0 | 1.0 | 1.0 |
| Coconut alcohol (C12/C18 fatty alcohol) | 1.0 | 1.0 | 1.0 | 1.0 |
| Methylparaben | 0.1 | 0.1 | 0.1 | 0.1 |
| Propylparaben | 0.1 | 0.1 | 0.1 | 0.1 |
| Cocoamidopropyl betaine (zwitterionic surfactant) | — | 3.0 | 3.0 | — |
| Ceteareth-12 (nonionic surfactant) | 1.5 | — | — | 1.5 |
| Ceteareth-20 (nonionic surfactant) | 1.5 | — | — | 1.5 |
| DD 1 (according to an exemplary embodiment of the present disclosure) | — | — | 1.0 | 1.0 |
| DD 2 (comparison) | 1.0 | 1.0 | — | — |
| Ammonium sulfate | 1.0 | 1.0 | 1.0 | 1.0 |
| Water | To 100 | To 100 | To 100 | To 100 |

The fatty alcohols (fatty substances) were melted together with the parabens. This melt was emulsified with the surfactants employed in each case and hot water; the dye predissolved in propylene glycol was then added, and the ammonium sulfate solution was added. The indicated pH value was adjusted with ammonia, and the mixture was then topped up to 100 g with water.

Colors

In each case, 1.8 g of the color cream was applied to an about 6 cm-long strand of human hair (Kerling European natural hair, 80% gray hair) and left there for 30 minutes at 30° C. After the contact time ended, the hair was rinsed, washed with a conventional hair washing product, and then dried. After drying, the color and color intensity of the strands were evaluated visually under the daylight lamp.

| Formulation | pH value | Shade | Color intensity |
|---|---|---|---|
| V1 | DD 2 (comparison) with nonionic surfactants | 9.5 | gray (initial hair color, no color absorption) | + |

-continued

| Formulation | pH value | Shade | Color intensity |
|---|---|---|---|
| V2 | DD 2 (comparison) with zwitterionic surfactant | 9.5 | gray (initial hair color, no color absorption) | + |
| V3 | DD 1 (DD according to an exemplary embodiment of the present disclosure) with zwitterionic surfactant | 9.5 | dark violet | ++++ |
| E1 | DD 1 (DD according an exemplary embodiment of the present disclosure) with nonionic surfactant | 9.5 | bluish black | +++++ |

Color intensity:
+ = poor
+++ = average
+++++ = very good

Formulations V1 and V2 are comparison formulations that did not contain direct dye DD 2 (DD 2: 3-methyl-2-(2-{4-[methyl({2-[methyl({4-[2-(3-methyl-1,3-thiazol-3-ium- 2-yl)diazen-1-yl]phenyl})amino]ethyl})amino]phenyl}diazen-1-yl)-1,3-thiazol-3-ium di(methyl sulfate) (comparison)).

No color absorption could be observed in the color of V1 and V2; the strands were dyed gray like the initial hair color (Kerling, 80% gray hair).

Formulation V3 is a comparison formulation, which in fact did contain a direct dye of the general formula (I), but instead of a nonionic surfactant contained the zwitterionic surfactant cocoamidopropyl betaine (alternative name: {[3-(dodecanoylamino)propyl](dimethyl)-ammonio}acetate), CAS No. 61789-40-0). The hair strands were dyed dark violet with this formulation.

Formulation E1 was a formulation in accordance with an exemplary embodiment of the present disclosure, which contains direct dye DD1 in combination with nonionic surfactants. (DD1=3-methyl-2-(2-{4-[methyl({3-[methyl({4-[2-(3-methyl-1,3-thiazol-3-ium-2-yl)diazen-1-yl]phenyl})amino]propyl})amino]phenyl}diazen-1-yl)-1,3-thiazol-3-ium, di(methyl sulfate)). An intense, deep dark blue, nearly black color without any red content was obtained.

The most intense coloring result could be achieved with formulation E1.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An agent for dyeing keratinic fibers comprising, in a cosmetic carrier,
   (a) at least one direct dye of the formula (I),

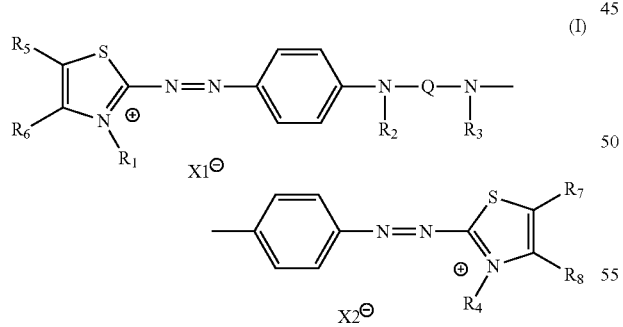

where
   R1, R4 independently of one another stand for a $C_1$-$C_6$ alkyl group, a $C_2$-$C_6$ alkenyl group, a hydroxy-$C_2$-$C_6$ alkyl group, a cyano-$C_1$-$C_6$ alkyl group, a halogen-$C_1$-$C_6$ alkyl group, an aryl-$C_1$-$C_6$ alkyl group, a heteroaryl-$C_1$-$C_6$ alkyl group, an aryl group, or a heteroaryl group,
   R2, R3 independently of one another stand for a hydrogen atom, $C_1$-$C_6$ alkyl group, a $C_2$-$C_6$ alkenyl group, a hydroxy-$C_2$-$C_6$ alkyl group, a cyano-$C_1$-$C_6$ alkyl group, a halogen-$C_1$-$C_6$ alkyl group, an aryl-$C_1$-$C_6$ alkyl group, a heteroaryl-$C_1$-$C_6$ alkyl group, an aryl group, or a heteroaryl group,
   R5, R6, R7, R8 independently of one another stand for a hydrogen atom, a $C_1$-$C_6$ alkyl group, a halogen atom from the group comprising chlorine, bromine, fluorine, or iodine, or for a $C_1$-$C_6$ alkoxy group,
   X1, X2 independently of one another stand for a physiologically acceptable anion, chloride, bromide, iodide, methyl sulfate, methyl sulfonate, p-toluenesulfonate, acetate, hydrogen sulfate, ½ sulfate, or ½ tetrachlorozincate,
   Q stands for a grouping of the formula (III), (IV), or (V),

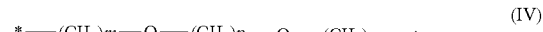
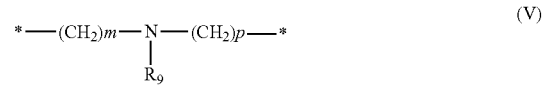

m, p, q each independently of one another stand for the numbers 2 or 3,
   R9 stands for a hydrogen atom, for a $C_1$-$C_6$ alkyl group, for a $C_2$-$C_6$ alkenyl group, or for a hydroxy-$C_2$-$C_6$ alkyl group,
   and
   (b) at least one nonionic surfactant.

2. The agent according to claim 1, wherein the agent comprises (a) at least one direct dye of the general formula (I), in which
   $R_1$, $R_4$ independently of one another stand for a $C_1$-$C_6$ alkyl group,
   $R_2$, $R_3$ independently of one another stand for a hydrogen atom or for a $C_1$-$C_6$ alkyl group,
   R5, R6, R7, R8 each stand for a hydrogen atom.

3. The agent according to claim 1, wherein the agent comprises (a) at least one direct dye of the general formula (I), which is selected from:
   salts of 3-methyl-2-(2-{4-[methyl({3-[methyl({4-[2-(3-methyl-1,3-thiazol-3-ium-2-yl)diazen-1-yl]phenyl})amino]propyl})amino]phenyl}diazen-1-yl)-1,3-thiazol-3-ium,
   salts of 3-methyl-2-{2-[4-({2-[2-({4-[2-(3-methyl-1,3-thiazol-3-ium-2-yl)diazen-1-yl]phenyl}amino)ethoxy]ethyl}amino)phenyl]diazen-1-yl}-1,3-thiazol-3-ium,
   salts of 3-methyl-2-(2-{4-[methyl(2-{2-[methyl({4-[2-(3-methyl-1,3-thiazol-3-ium-2-yl)diazen-1-yl]phenyl})amino]ethoxy}ethyl)amino]phenyl}diazen-1-yl)-1,3-thiazol-3-ium,
   salts of 2-(2-{4-[ethyl(2-{2-[ethyl({4-[2-(3-methyl-1,3-thiazol-3-ium-2-yl)diazen-1-yl]phenyl})amino]ethoxy}ethyl)amino]phenyl}diazen-1-yl)-3-methyl-1,3-thiazol-3-ium,
   salts of 3-ethyl-2-{2-[4-({2-[2-({4-[2-(3-ethyl-1,3-thiazol-3-ium-2-yl)diazen-1-yl]phenyl}amino)ethoxy]ethyl}amino)phenyl]diazen-1-yl}-1,3-thiazol-3-ium,
   salts of 3-ethyl-2-{2-[4-({2-[2-({4-[2-(3-ethyl-1,3-thiazol-3-ium-2-yl)diazen-1-yl]phenyl}(methyl)amino)ethoxy]ethyl}(methyl)amino)phenyl]diazen-1-yl}-1,3-thiazol-3-ium,
   salts of 3-ethyl-2-(2-{4-[ethyl(2-{2-[ethyl({4-[2-(3-ethyl-1,3-thiazol-3-ium-2-yl)diazen-1-yl]phenyl})amino]ethoxy}ethyl)amino]phenyl}diazen-1-yl)-1,3-thiazol-3-ium, salts of 3-methyl-2-{2-[4-(10-{4-[2-(3-methyl-1,3-thiazol-3-ium-2-yl)diazen-1-yl]phenyl}-4,7-dioxa-1,10-diazadecan-1-yl)phenyl]diazen-1-yl}-1,3-thiazol-3-ium, salts of 3-methyl-2-{2-[4-(11-{4-[2-(3-methyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium, salts of 3-methyl-2-{2-[4-(12-{4-[2-(3-methyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium, salts of 3-ethyl-2-{2-[4-(10-{4-[2-(3-ethyl-1,3-thiazol-3-ium-2-yl)diazen-1-yl]phenyl}-4,7-dioxa-1,10-diazadecan-1-yl)phenyl]diazen-1-yl}-1,3-thiazol-3-ium, salts of 3-ethyl-2-{2-[4-(11-{4-[2-(3-ethyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium, and/or salts of 3-ethyl-2-({2-[4-(12-({4-[2-(3-ethyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium.

4. The agent according to claim 1, wherein, based on the total weight of the agent, the agent contains one or more direct dyes (a) of the formula (I) in a total amount of 0.01 to 4.5% by weight.

5. The agent according to claim 1, wherein the agent comprises (b) at least one nonionic surfactant, which is selected from:
  adducts of 2 to 100 mol of ethylene oxide and/or 2 to 100 mol of propylene oxide to linear and branched fatty alcohols having 12 to 30 C atoms, fatty alcohol polyglycol ethers or fatty alcohol polypropylene glycol ethers or mixed fatty alcohol polyethers,
  adducts of 2 to 100 mol of ethylene oxide and/or 2 to 100 mol of propylene oxide to linear and branched fatty acids having 12 to 30 C atoms, fatty acid polyglycol ethers or fatty acid polypropylene glycol ethers or mixed fatty acid polyethers, and
  adducts of 5 to 60 mol of ethylene oxide to castor oil and hydrogenated castor oil.

6. The agent according to claim 1, wherein the agent comprises as nonionic surfactant (b) at least one compound of the formula (B1) and/or at least one compound of the formula (B2),

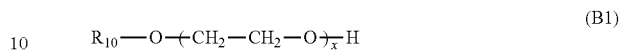

(B1)

where
R10 stands for a linear or branched $C_{12}$-$C_{30}$ alkyl group and
x stands for an integer from 2 to 100,

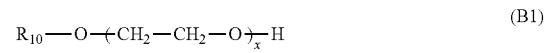

(B1)

where
R11 stands for a linear or branched $C_{11}$-$C_{29}$ alkyl group and
y stands for an integer from 2 to 100.

7. The agent according to claim 1, wherein the agent comprises as nonionic surfactant (b) at least one compound of the formula (B1),

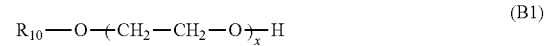

(B1)

where
R10 stands for a linear or branched $C_{12}$-$C_{30}$ alkyl group and
x stands for an integer from 10 to 50.

* * * * *